(12) United States Patent
Sato

(10) Patent No.: US 9,687,238 B2
(45) Date of Patent: Jun. 27, 2017

(54) IMPLANT PLACEMENT DEVICE

(71) Applicant: OLYMPUS CORPORATION, Tokyo (JP)

(72) Inventor: Masatoshi Sato, Yokohama (JP)

(73) Assignee: OLYMPUS CORPORATION, Tokyo (JP)

( * ) Notice: Subject to any disclaimer, the term of this patent is extended or adjusted under 35 U.S.C. 154(b) by 386 days.

(21) Appl. No.: 13/894,551

(22) Filed: May 15, 2013

(65) Prior Publication Data

US 2013/0325038 A1 Dec. 5, 2013

Related U.S. Application Data

(63) Continuation of application No. PCT/JP2012/077098, filed on Oct. 19, 2012.

(60) Provisional application No. 61/556,449, filed on Nov. 7, 2011.

(51) Int. Cl.
| | | |
|---|---|---|
| *A61B 17/11* | (2006.01) | |
| *A61B 17/34* | (2006.01) | |
| *A61B 17/068* | (2006.01) | |
| *A61B 17/06* | (2006.01) | |

(Continued)

(52) U.S. Cl.
CPC ............ *A61B 17/11* (2013.01); *A61B 17/068* (2013.01); *A61B 17/3468* (2013.01); *A61B 17/3478* (2013.01); *A61B 2017/00367* (2013.01); *A61B 2017/00477* (2013.01); *A61B 2017/0649* (2013.01); *A61B 2017/06171* (2013.01)

(58) Field of Classification Search
CPC ... A61B 17/11; A61B 17/068; A61B 17/3478; A61B 17/3468; A61B 2017/0649; A61B 2017/00367; A61B 2017/00477; A61B 2017/06171
USPC ........................................................ 606/139
See application file for complete search history.

(56) References Cited

U.S. PATENT DOCUMENTS

| 5,582,616 A | * | 12/1996 | Bolduc et al. ................ 606/143 |
| 2010/0010509 A1 | * | 1/2010 | Ishioka et al. ................ 606/139 |

FOREIGN PATENT DOCUMENTS

| JP | 2002-512550 A | 4/2002 |
| JP | 2004-508093 A | 3/2004 |
| JP | 2005-193044 A | 7/2005 |

(Continued)

OTHER PUBLICATIONS

International Search Report PCT/JP2012/077098 dated Jan. 15, 2013.

Primary Examiner — Corrine McDermott
Assistant Examiner — Tin Nguyen
(74) Attorney, Agent, or Firm — Scully, Scott, Murphy & Presser, PC

(57) ABSTRACT

An implant placement device includes a longitudinal axis member having a lumen extending along a longitudinal axis of the longitudinal axis member such that the implant is disposed in a stretched state and an opening formed by communicating with the lumen, a stylet provided in the lumen, a sheath into which the longitudinal axis member is inserted,—an operating part operating the sheath so as to be rotatable around the longitudinal axis, and having a contact surface that is in contact with a part of the implant, which is pushed out of the opening of the longitudinal axis member by the stylet, in a rotational direction around the longitudinal (Continued)

axis in a state where the opening of the longitudinal axis member is located inside the sheath.

7 Claims, 30 Drawing Sheets

(51) Int. Cl.
  *A61B 17/00* (2006.01)
  *A61B 17/064* (2006.01)

(56) References Cited

FOREIGN PATENT DOCUMENTS

| | | | |
|---|---|---|---|
| JP | 2008-504943 | A | 2/2008 |
| JP | 2009-66408 | A | 4/2009 |
| JP | 2010-17541 | A | 1/2010 |
| JP | 4801230 | B2 | 10/2011 |
| WO | 99/21490 | A1 | 5/1999 |
| WO | 02/19923 | A1 | 3/2002 |
| WO | 2005/115256 | A2 | 12/2005 |

* cited by examiner

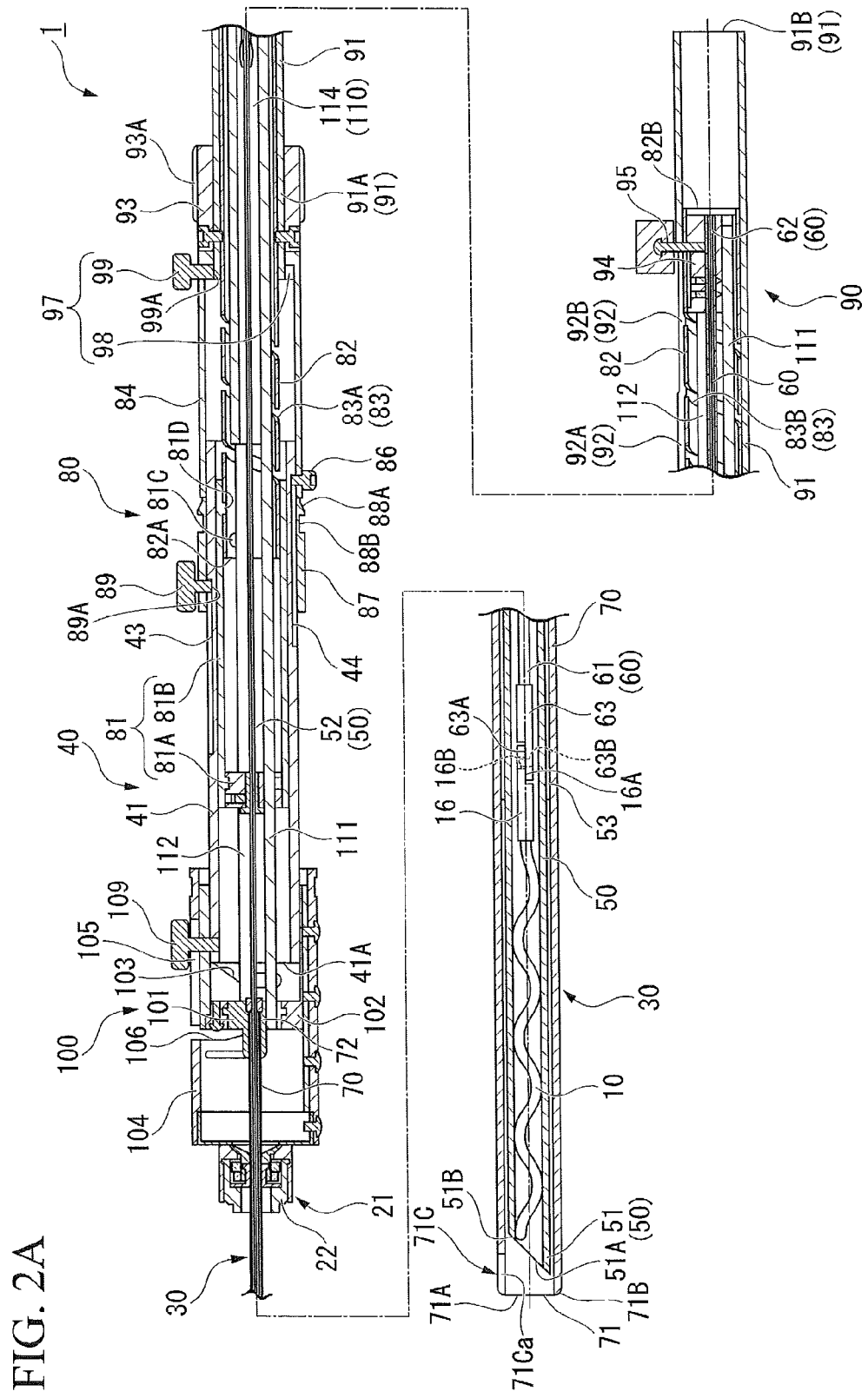

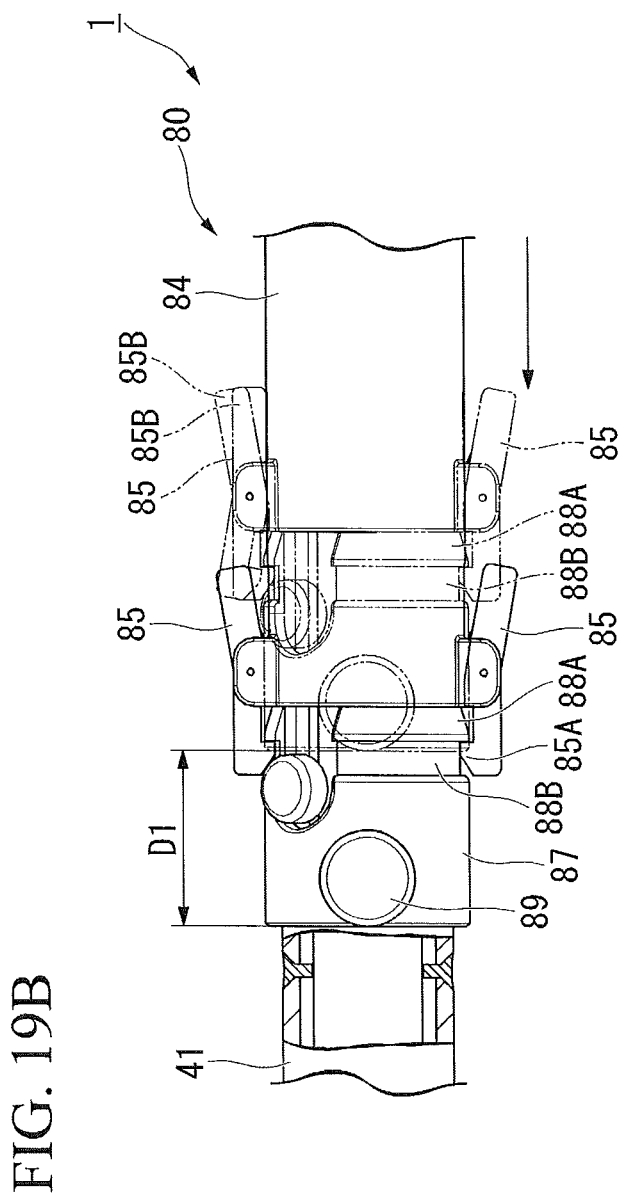

IMPLANT PLACEMENT DEVICE

Priority is claimed on U.S. Provisional Application No. 61/556,449, filed on Nov. 7, 2011 and PCT Application No. PCT/JP2012/077098, filed on Oct. 19, 2012, the contents of which are incorporated herein by reference.

BACKGROUND OF THE INVENTION

Field of the Invention

The present invention relates, generally, to an implant placement device and, more particularly, to an implant placement device that endoscopically places an implant in tissue.

Description of Related Art

As a method of performing a treatment on organs of a human body, laparoscopic surgery is known in which a treatment tool is percutaneously inserted. The laparoscopic surgery requires less invasiveness compared to a case of making an incision in the abdomen, and fast recovery can be expected.

The treatment tool used in the laparoscopic surgery has a hard shaft that is percutaneously inserted into the body. A treatment tool such as forceps which is used to perform a treatment on living tissues is provided at a distal end of the shaft. For example, in Japanese Unexamined Patent Application, First Publication No. 2005-193044, a treatment tool used to join luminal organs is disclosed. An intraluminal anastomosis device that is the treatment tool disclosed in Japanese Unexamined Patent Application, First Publication No. 2005-193044 is mounted with a gripping tool, which is freely opened and closed, at a distal end of a shaft. A clamp is inserted into the shaft. The clamp may be pushed out of the distal end of the shaft by an extrusion mechanism of a proximal end. The clamp is produced by performing a heat treatment on a shape-memory alloy in a flat coil shape, and is inserted into the shaft in an extended state. When the clamp is used, the clamp is pushed out by the extrusion mechanism and is inserted into the body. The clamp is heated by body heat, is restored to the coil shape, and is placed in the living tissue. The luminal organs can be anastomosed by the clamp restored to the coil shape.

As another example of placing the clamp in the living tissue, a surgical tissue fastening instrument is disclosed in PCT International Publication No. WO2002/019923. For example, the clamp is pushed out of a needle and is placed in the tissue. The tissue fastening instrument is provided with a stopper that controls the depth to which the needle is inserted into the tissue and an amount at which the clamp is supplied into the tissue. When a treatment is performed using the tissue fastening instrument, the instrument housing the clamp and the needle is caused to strike the tissue. After the needle is advanced and inserted into the tissue, the clamp is fixed at a position by the stopper. Afterwards, the needle is pulled out of the tissue. Since the clamp is not displaced due to the presence of the stopper, a distal end portion of the clamp remains inside the tissue. When the instrument is removed from the tissue, the rest of the clamp remains outside the tissue. When the clamp is restored to the coil shape, the tissue is clamped.

SUMMARY OF THE INVENTION

According to a first aspect of the present invention, an implant placement device which is used to place an implant formed of a coil-shaped metal wire into a body includes a long shaft member having a lumen extending along its own longitudinal axis such that the implant is disposed in a stretched state and an opening formed by communicating with the lumen, a stylet installed in the lumen so as to be movable in the lumen in a direction parallel with the longitudinal axis in order to push the implant out of the long shaft member, a tubular sheath which is installed so as to be rotatable around the longitudinal axis and into which the long shaft member is inserted, an operating part installed at a proximal end side of the sheath which makes the sheath rotatable around the longitudinal axis, and a contact part which is installed at a distal end of the sheath so as to rotate the implant depending on the operation of the operating part and which has a contact surface that is in contact with a part of the implant, which is pushed out of the opening of the long shaft member by the stylet, in a rotational direction around the longitudinal axis in a state in which the opening of the long shaft member is located inside the sheath.

According to a second aspect of the present invention, in the implant placement device according to the first aspect of the present invention, the contact part may be a notch formed in the distal end of the sheath.

According to a third aspect of the present invention, in the implant placement device according to the second aspect of the present invention, the stylet may be a rod-shaped member configured so that a distal end of the stylet is in contact with a proximal end of the implant.

According to a fourth aspect of the present invention, the implant placement device according to the second aspect of the present invention may further include a coupling portion which is formed at a distal end of the stylet, which is detachably coupled with the implant, which moves along with the stylet and the implant in the direction parallel with the longitudinal axis depending on the operation of the operating part, and which is rotated around the longitudinal axis. The stylet may be rotatable around the longitudinal axis.

According to a fifth aspect of the present invention, in the implant placement device according to the second aspect of the present invention, the operating part may include a rotation interlocking mechanism that cooperates with the rotation of the sheath around the longitudinal axis and rotates the stylet around a central axis of the stylet.

According to a sixth aspect of the present invention, in the implant placement device according to the second aspect of the present invention, the notch may have a surface with which the implant is in contact.

According to a seventh aspect of the present invention, in the implant placement device according to the second aspect of the present invention, the notch may open at the distal end of the sheath. The notch may include a pair of opposite surfaces spaced apart from each other while extending in the direction parallel with the longitudinal axis. A first opposite surface of the pair of opposite surfaces may be provided with a projection that projects toward the second opposite surface of the pair of opposite surfaces. The first opposite surface may be located at a proximal side of a rotation direction of the sheath relative to the second opposite surface, and the first opposite surface may be located at a distal side of a rotation direction of the sheath relative to the second opposite surface.

According to an eighth aspect of the present invention, in the implant placement device according to the seventh aspect of the present invention, the surface of a proximal end side of the projection may be an inclined surface that is inclined so as to be directed in the rotational direction of the sheath with the approach to the distal end side of the sheath.

According to a ninth aspect of the present invention, in the implant placement device according to the second aspect of the present invention, the notch may be open on only on place in a distal end surface of the sheath.

According to a tenth aspect of the present invention, in the implant placement device according to the second aspect of the present invention, the notch may have a width greater than the diameter of the metal wire.

BRIEF DESCRIPTION OF THE DRAWINGS

FIG. 2A is a cross-sectional view showing the implant placement device according to the embodiment of the present invention;

FIG. 19B is a motion explanatory view which shows the movement of the tubular member operating part when the implant placement device according to the embodiment of the present invention is used;

DETAILED DESCRIPTION OF THE INVENTION

Hereinafter, an implant placement device according to an embodiment of the present invention will be described.

Figure 1:
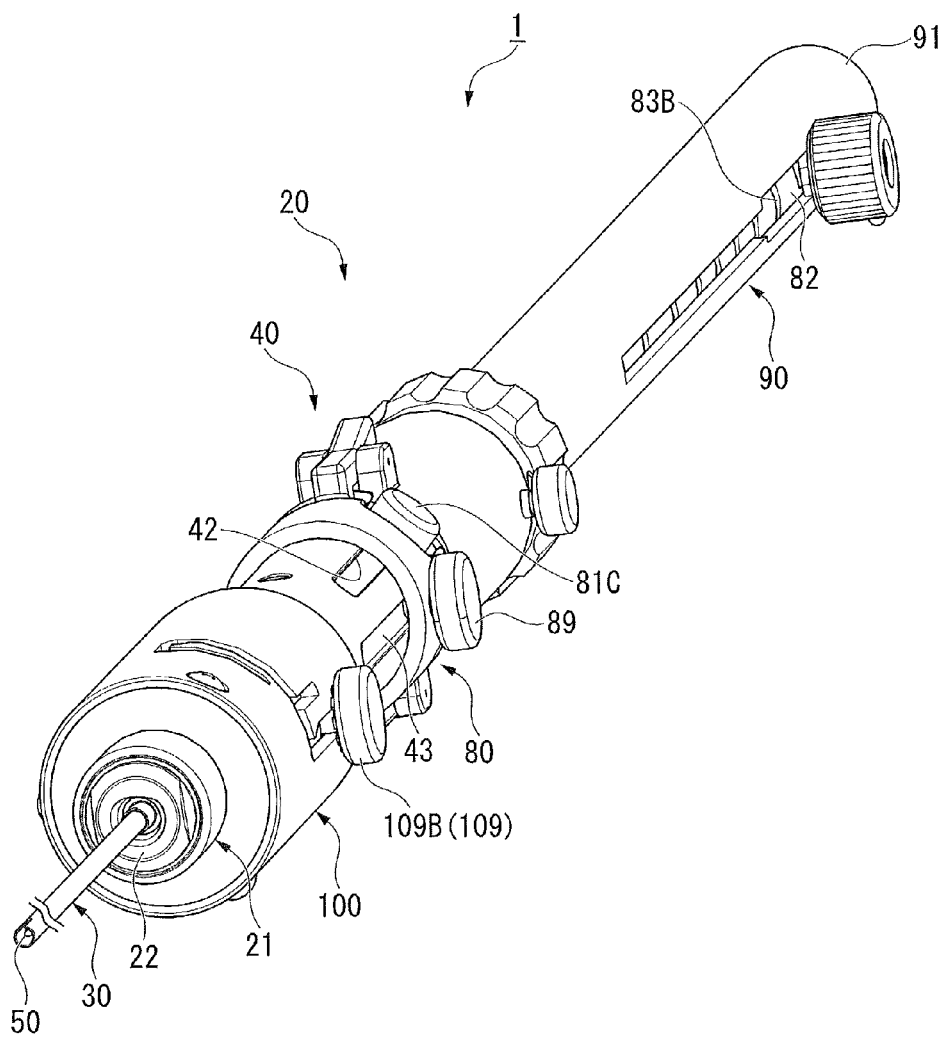
FIG. 1 is a perspective view showing an implant placement device according to an embodiment of the present invention.
Figure 2B:
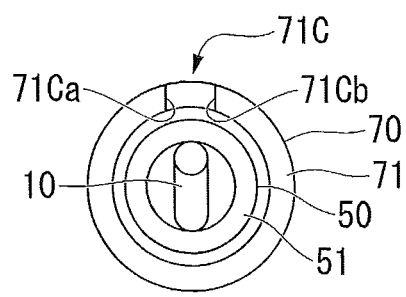
FIG. 2B is a view showing a sheath of the implant placement device according to the embodiment of the present invention when viewed from a distal end thereof.
Figure 2C:
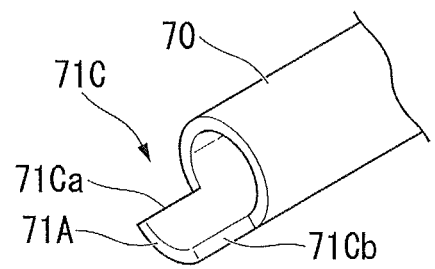
FIG. 2C is a perspective view showing the distal end of the sheath of the implant placement device according to the embodiment of the present invention.
Figure 3:
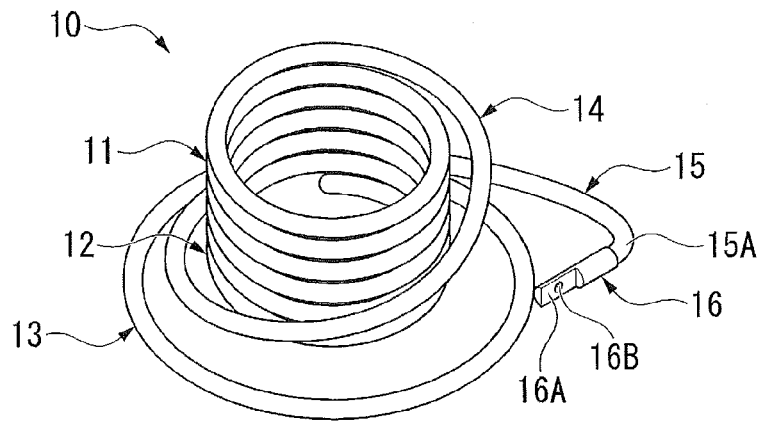
FIG. 3 is a perspective view showing a tissue fastener of the implant placement device according to the embodiment of the present invention.
Figure 4A:
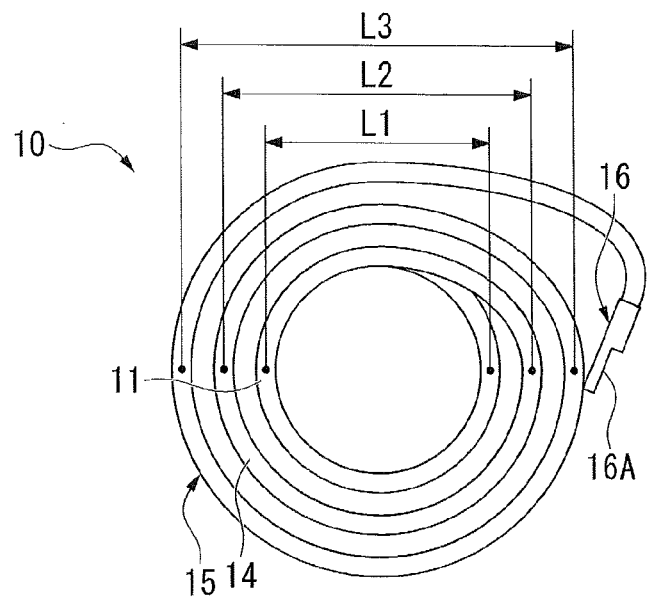
FIG. 4A is a plan view showing the tissue fastener of the implant placement device according to the embodiment of the present invention.
Figure 4B:
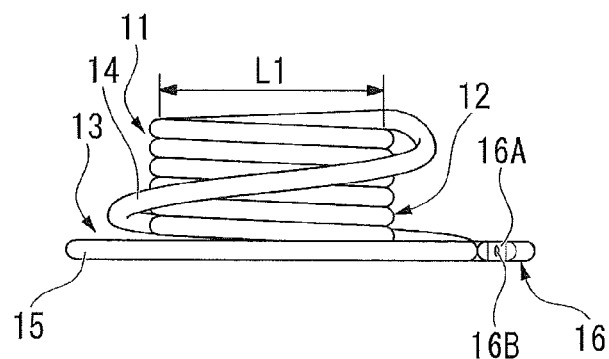
FIG. 4B is a side view showing the tissue fastener of the implant placement device according to the embodiment of the present invention.
Figure 5A:
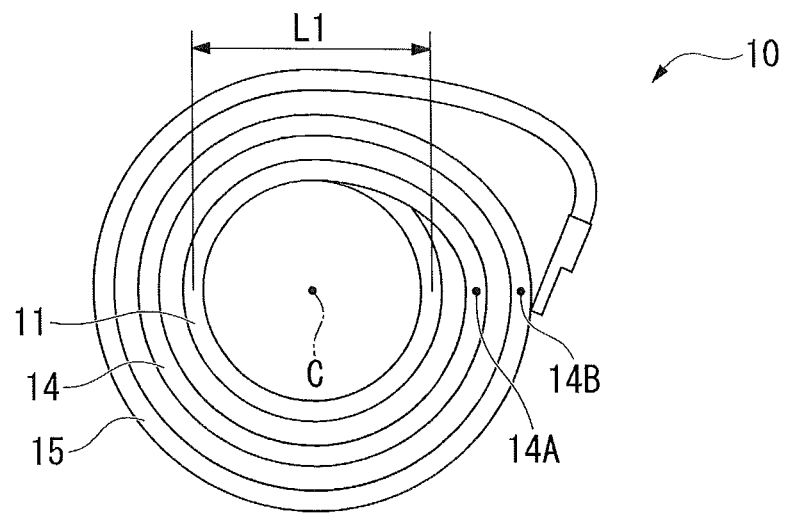
FIG. 5A is a plan view showing the tissue fastener of the implant placement device according to the embodiment of the present invention.
Figure 5B:
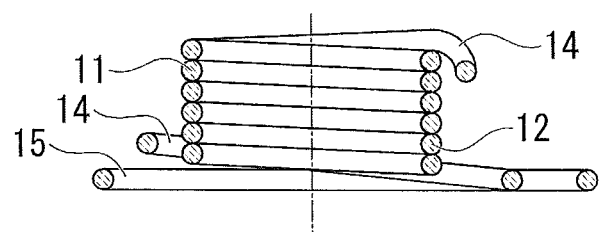
FIG. 5B is a side cross-sectional view showing the tissue fastener of the implant placement device according to the embodiment of the present invention.
Figure 5C:
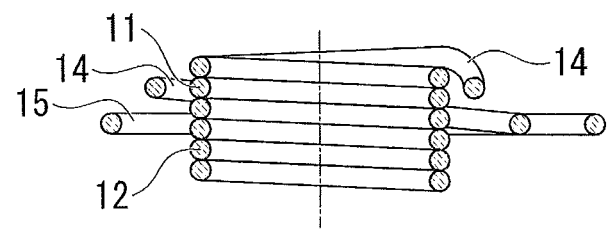
FIG. 5C is a cross-sectional view showing a shape of the tissue fastener when the tissue fastener of the implant placement device according to the embodiment of the present invention is placed in living tissue.
Figure 5D:
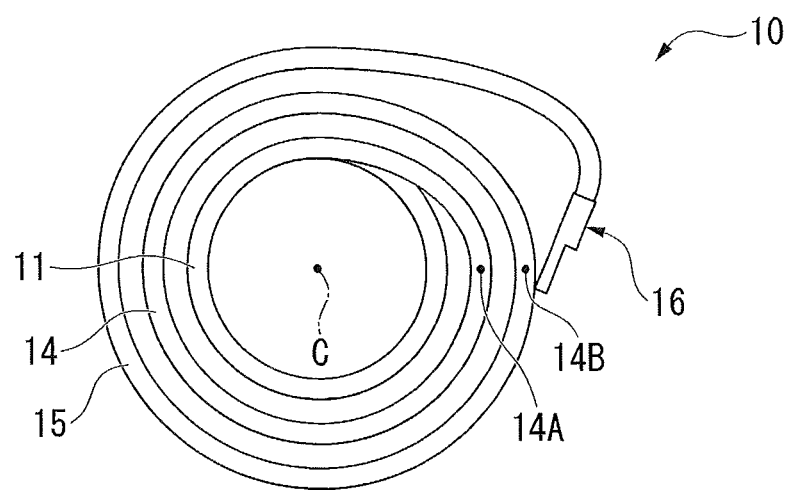
FIG. 5D is a plan view showing the tissue fastener of the shape shown in FIG. 5C.
Figure 6:
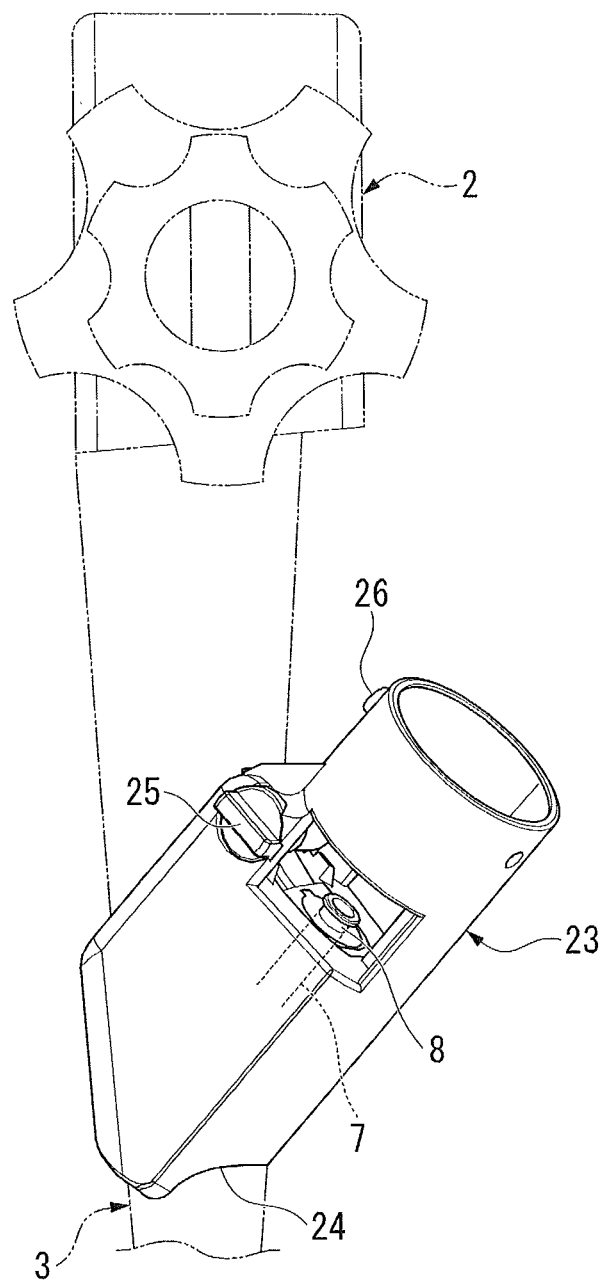
FIG. 6 is a perspective view showing a state in which the implant placement device according to the embodiment of the present invention is mounted on an endoscope.
Figure 7A:
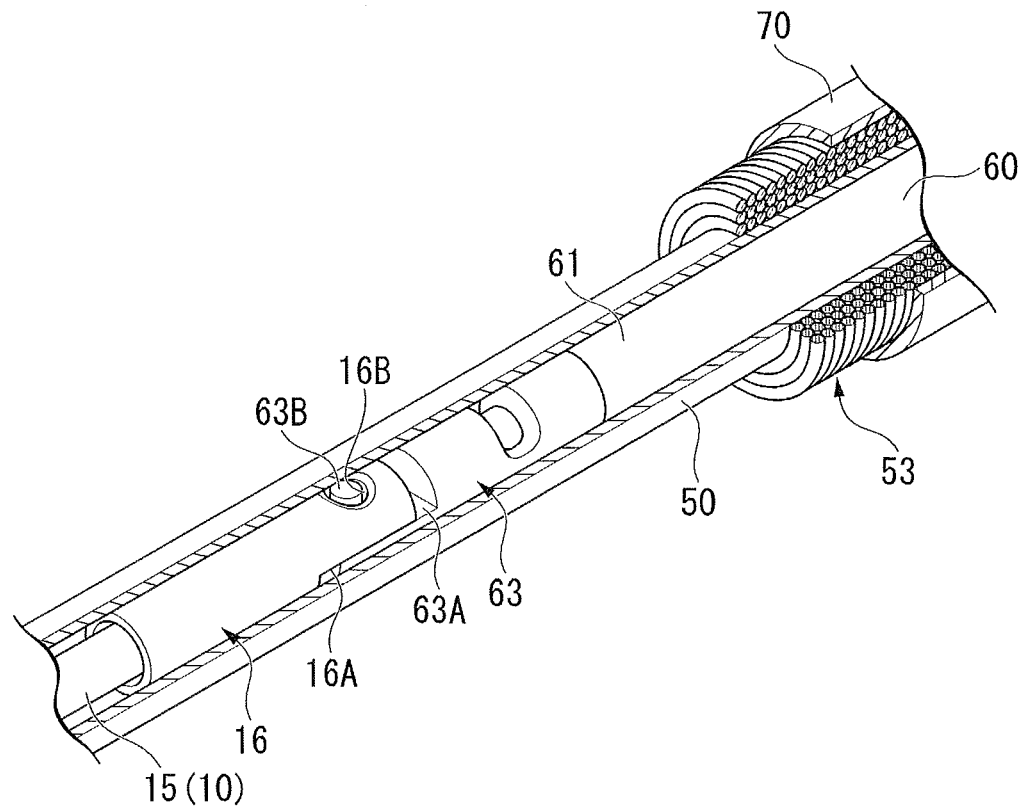
FIG. 7A is a partial cross-sectional view showing a configuration of a part of an insertion part of the implant placement device according to the embodiment of the present invention.
Figure 7B:
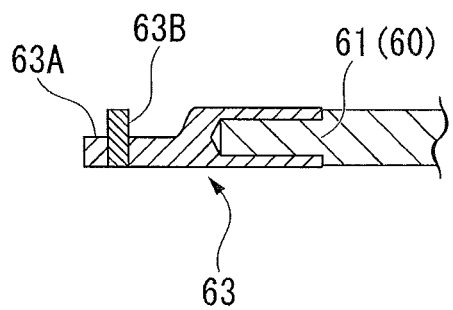
FIG. 7B is an enlarged cross-sectional view showing a configuration of a part of a stylet in the implant placement device according to the embodiment of the present invention.
Figure 8:
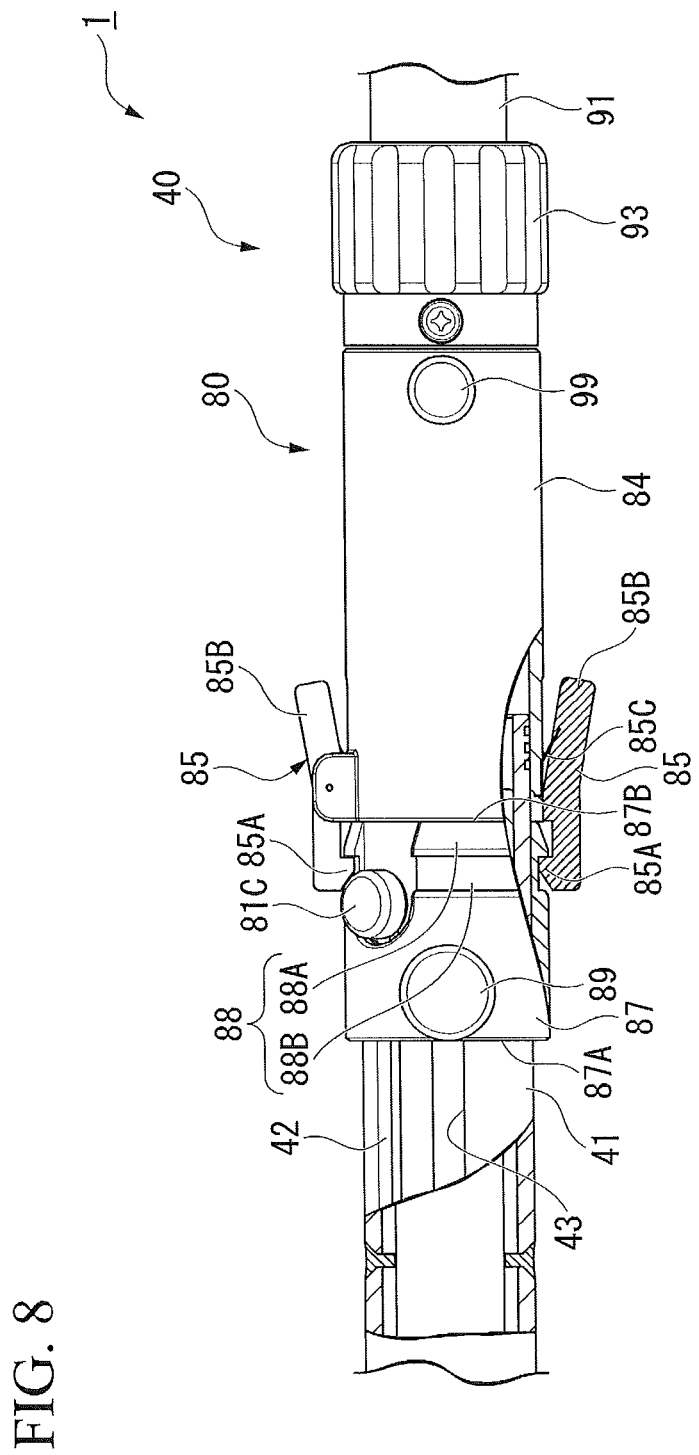
FIG. 8 is an enlarged partial cross-sectional view showing a portion of a tubular member operating part in the implant placement device according to the embodiment of the present invention.
Figure 9:
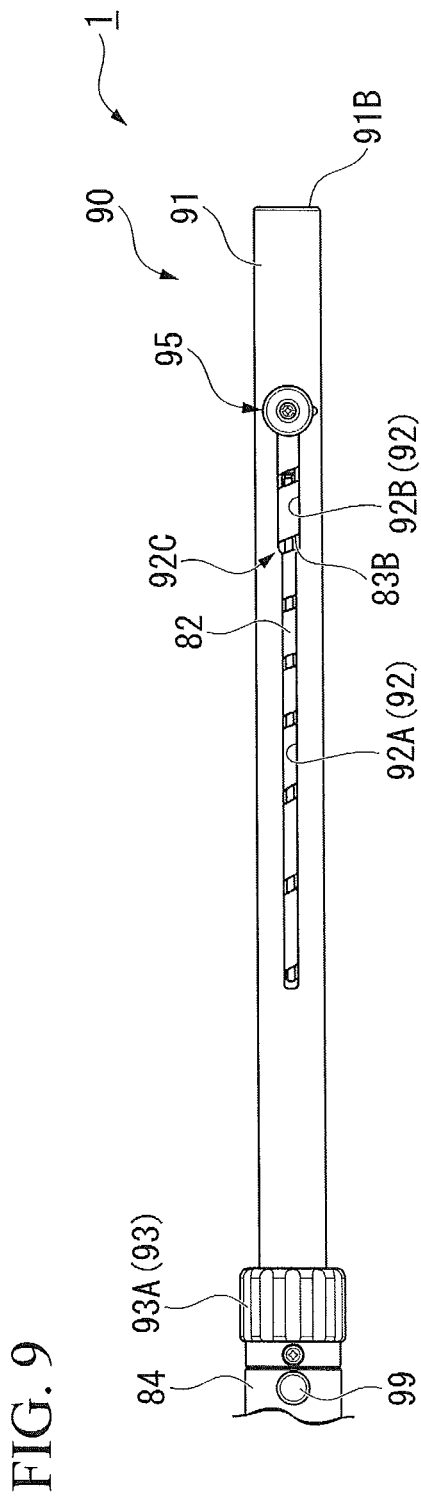
FIG. 9 is an enlarged side view showing a portion of a stylet operating part in the implant placement device according to the embodiment of the present invention.
Figure 10A:
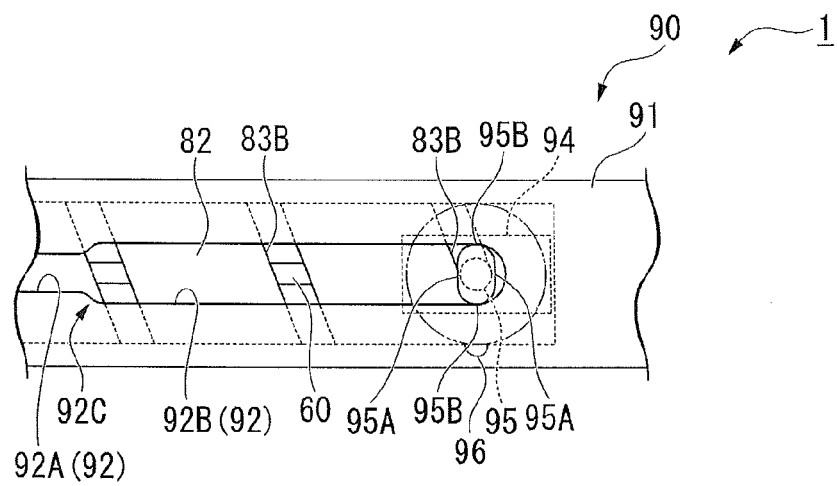
FIG. 10A is an enlarged side view showing a configuration of a part of the stylet operating part in the implant placement device according to the embodiment of the present invention.
Figure 10B:
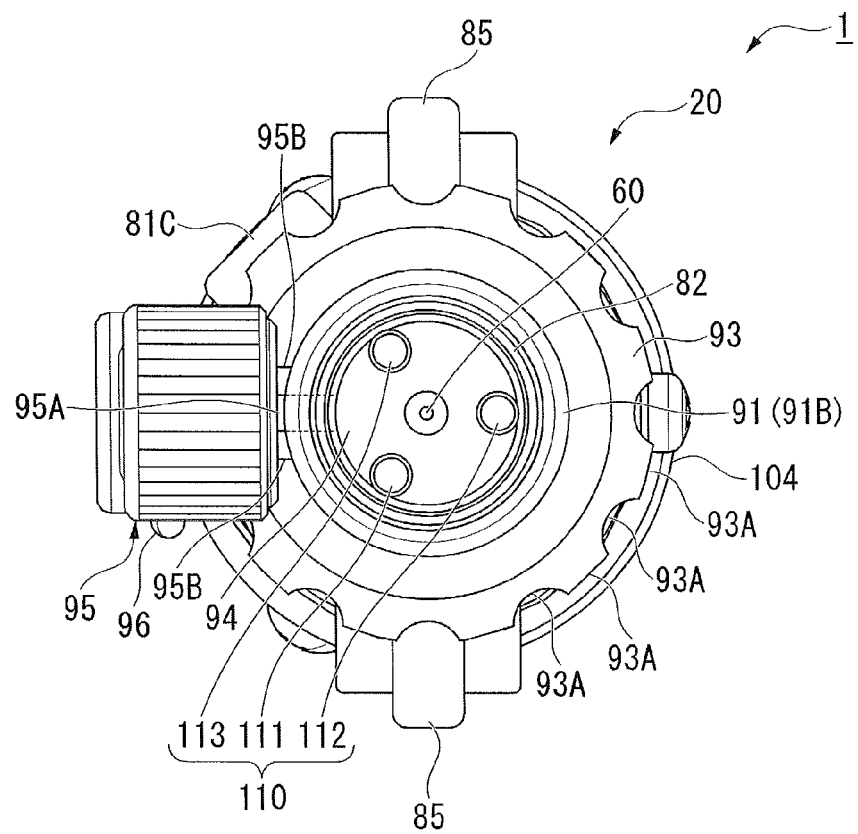
FIG. 10B is a rear view showing a part of the stylet operating part in the implant placement device according to the embodiment of the present invention when viewed from a proximal end side of an sheath tube.
Figure 11:
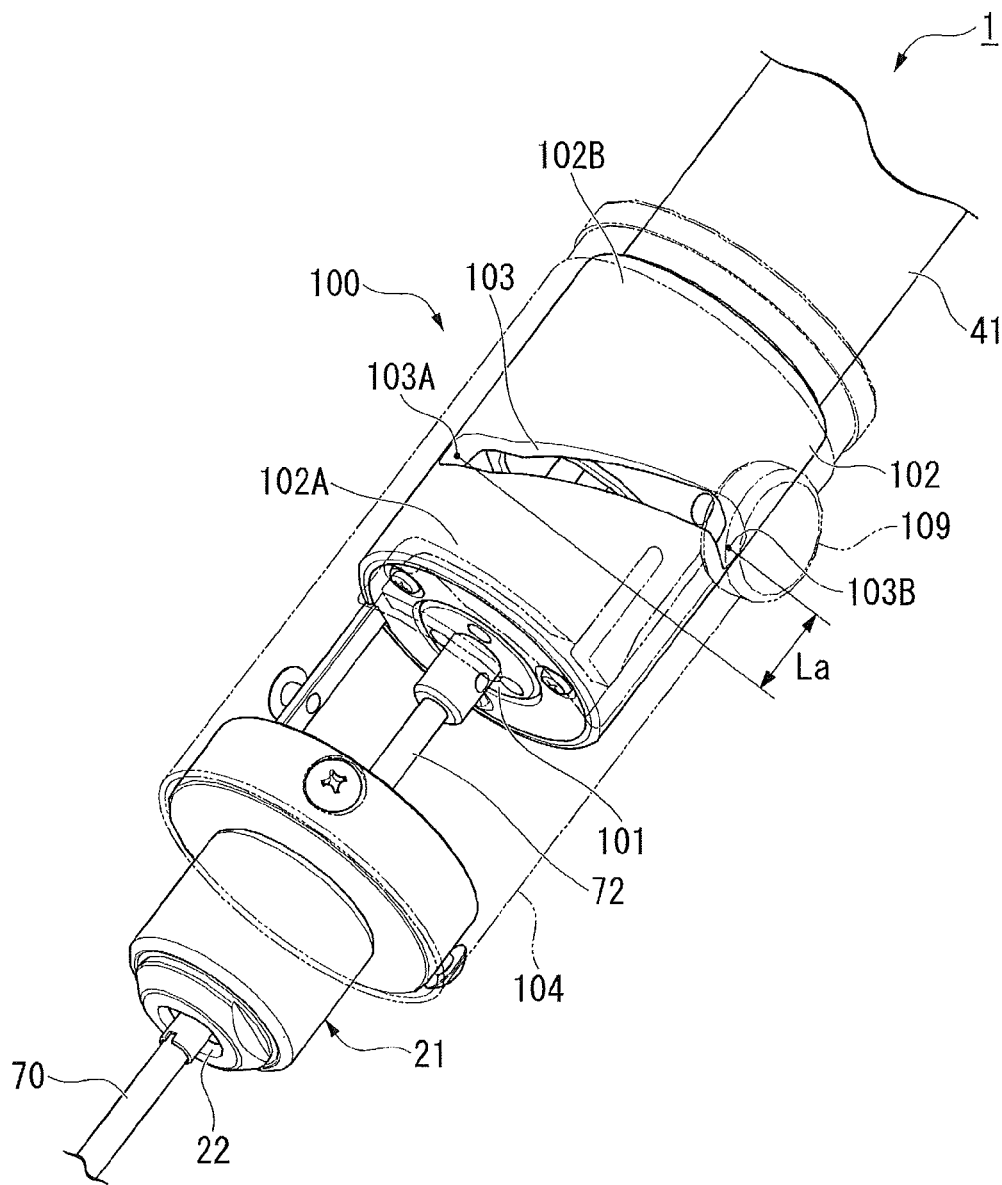
FIG. 11 is an enlarged perspective view showing a configuration of a portion of a sheath operating part in the implant placement device according to the embodiment of the present invention.
Figure 12:
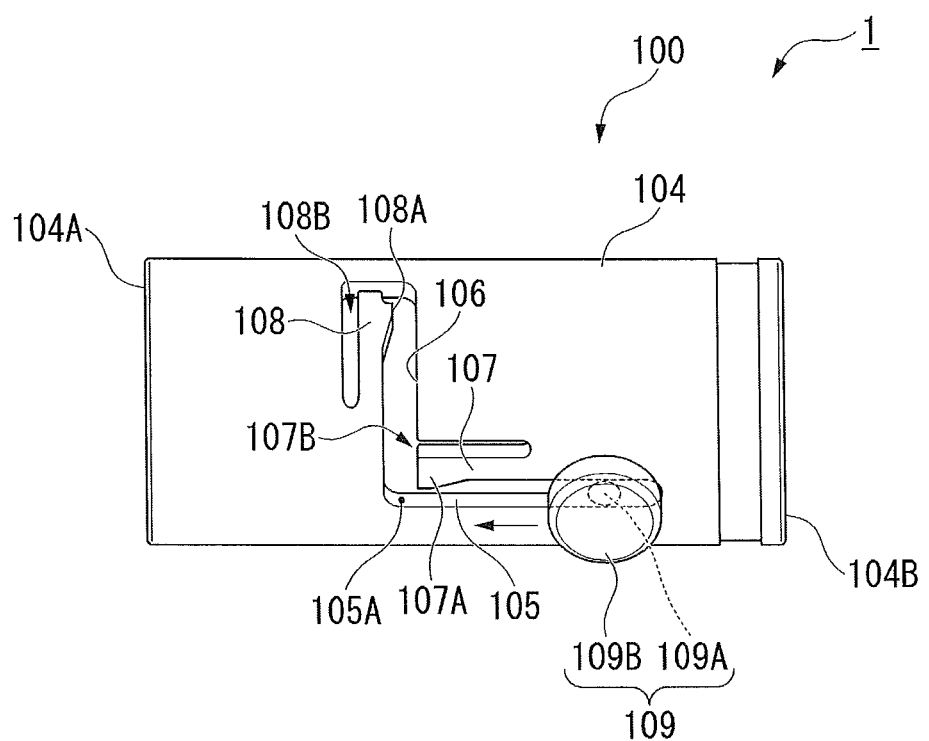
FIG. 12 is a side view showing a configuration of a part of the sheath operating part in the implant placement device according to the embodiment of the present invention.
Figure 13:
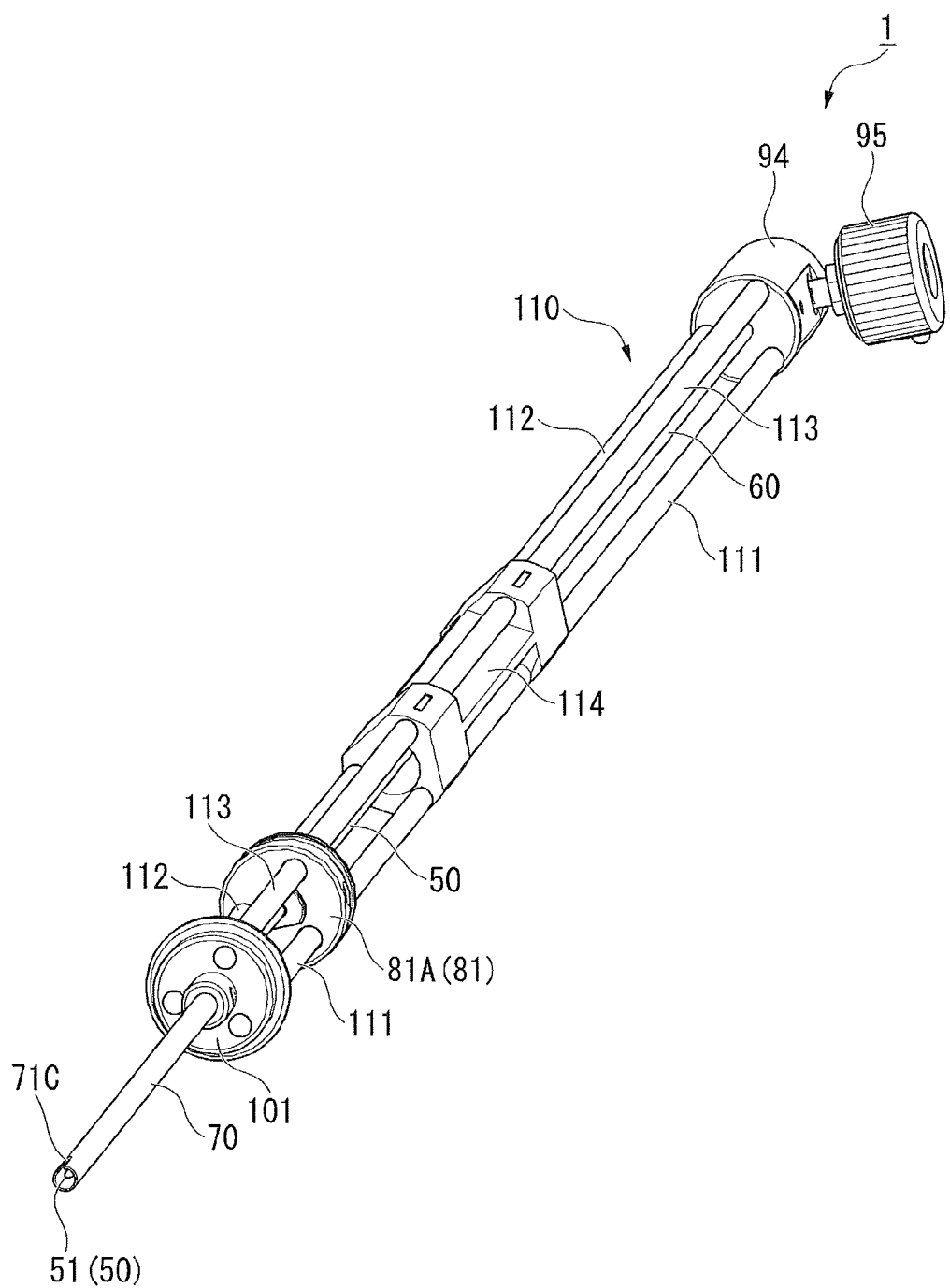
FIG. 13 is a perspective view showing a configuration of a rotation interlocking mechanism in the implant placement device according to the embodiment of the present invention.

A configuration of the implant placement device of the present embodiment will be described with reference to FIGS. 1 to 13. FIG. 1 is a perspective view showing an implant placement device 1. FIG. 2A is a cross-sectional view showing the implant placement device 1. FIG. 2B is a view showing a sheath 70 of the implant placement device 1 when viewed from a distal end. FIG. 2C is a perspective view showing a distal end of the sheath 70 of the implant placement device 1. FIG. 3 is a perspective view showing a tissue fastener 10 of the implant placement device 1. FIG. 4A is a plan view of the tissue fastener 10. FIG. 4B is a side view of the tissue fastener 10. FIGS. 5A to 5D are views showing the tissue fastener 10. FIG. 5A is a plan view of the tissue fastener 10, FIG. 5B is a side cross-sectional view of the tissue fastener 10, FIG. 5C is a cross-sectional view showing a shape of the tissue fastener 10 when the tissue fastener 10 is placed in living tissue, and FIG. 5D is a plan view showing the tissue fastener 10 having the shape shown in FIG. 5C. FIG. 6 is a perspective view showing a state in which the implant placement device 1 is mounted on an endoscope 2. FIGS. 7A and 7B are views showing a configuration of a part of an insertion part 30 of the implant placement device 1, wherein FIG. 7A is a partial cross-sectional view and FIG. 7B is an enlarged cross-sectional view showing a configuration of a part of a stylet 60. FIG. 8 is an enlarged, partial cross-sectional view showing a tubular member operating part 80 in the implant placement device 1. FIG. 9 is an enlarged side view showing a stylet operating part 90 in the implant placement device 1. FIGS. 10A and 10B are enlarged views showing a configuration of a part of the stylet operating part 90, wherein FIG. 10A is a side view and FIG. 10B is a rear view viewed from a proximal end 91B of a sheath tube 91. FIG. 11 is an enlarged perspective view showing a configuration of a sheath operating part 100 in the implant placement device 1. FIG. 12 is a side view showing a configuration of a part of the sheath operating part 100. FIG. 13 is a perspective view showing a configuration of a rotation interlocking mechanism 110 in the implant placement device 1.

As shown in FIGS. 1 and 2, the implant placement device 1 is equipped with an applicator 20 used to place a tissue fastener 10, which is an implant placed in the body, in the body. Further, the implant placement device 1 may be equipped with the tissue fastener 10.

The implant placement device 1 of the present embodiment is a device that performs a treatment of integrally fastening first and second living tissues together and establishing a fistula in a portion where both of the tissues are fastened. Here, the first and second living tissues are not limited to referring to different organs. For example, a certain area of a certain organ is set as the first living tissue, and another area of the same organ is treated as the second living tissue. A case of clamping these two areas is also included. In the present embodiment, a treatment of clamping the common bile duct as the second living tissue to the duodenum as the first living tissue and spatially connecting both of the organs is given as an example, and the implant placement device of the present embodiment will be described based on this treatment.

First, the tissue fastener 10 that is the implant in the implant placement device 1 of the present embodiment will be described.

FIGS. 3 to 5D are views showing the tissue fastener 10 of the present embodiment. As shown in FIG. 3, the tissue fastener 10 includes a first tissue fixing section 11, a second tissue fixing section 12, and an outer peripheral spring section 13. The first tissue fixing section 11 is retained on the duodenum. The second tissue fixing section 12 is retained on the common bile duct adjacent to the duodenum. The outer peripheral spring section 13 is connected to the first tissue fixing section 11.

All the parts of the tissue fastener 10, i.e. the first tissue fixing section 11, the second tissue fixing section 12, and the outer peripheral spring section 13, are formed of one highly elastic metal wire (hereinafter, simply referred to as a "metal wire") wound in a coil shape. Alternatively, this metal wire may be formed of a superelastic alloy having superelasticity. The first and second tissue fixing sections 11 and 12 have the same loop diameter, and are formed so that the mutual loops become coaxial. In the present embodiment, in the metal wire of the tissue fastener 10, a portion on which the duodenum and the common bile duct are retained is sinistrally coiled.

The outer peripheral spring section 13 includes a spring portion 14 and an end coil portion 15. The spring portion 14 extends from an end of the first tissue fixing section 11. The end coil portion 15 extends from an end of the spring portion 14.

The spring portion 14 extends from the end of the first tissue fixing section 11 toward the second tissue fixing section 12 while forming a greater loop than the first and second tissue fixing sections 11 and 12. The loop which the spring portion 14 forms is gradually increased with the approach to a side of the second tissue fixing section 12. However, this shape is not essential in the present embodiment. For example, the spring portion 14 may extend toward the second tissue fixing section 12 while forming a loop having the same diameter.

Since the spring portion 14 extends toward the second tissue fixing section 12, as shown in FIGS. 4A and 4B, the metal wire forming the spring portion 14 has an angle so as to be inclined with respect to the loops of the first and second tissue fixing sections 11 and 12 (hereinafter referred to as a "basic loop L1").

The spring portion 14 may be formed so as to have an integer of windings in one or more rotations. The term "integer of windings in one rotation" means that, when viewed from the top of the tissue fastener 10 as shown in FIG. 5A, an end 14A of the spring portion 14 which is located at the side of the first tissue fixing section 11 and an end 14B of the spring portion 14 which is located at the side of the end coil portion 15 do not sandwich the center C of the basic loop L1 therebetween but stand abreast of the center C on the same line as the center C.

When the spring portion 14 has an integer of one or more windings, the spring portion 14 is evenly distributed at a radial outer side of the basic loop L1 as in FIG. 5B regardless of a cross section when the tissue fastener 10 is viewed from an axial cross section that passes through the center C. In FIG. 5B, a state in which the spring portion 14 is set to one winding is shown as an example. As long as the spring portion 14 has the integer of windings, a similar effect is produced even when the spring portion 14 is set to two or more windings. Thus, the force which the spring portion 14 exerts on the first and second tissue fixing sections 11 and 12 in a radial direction of the basic loop L1 becomes uniform. For this reason, as shown in FIGS. 5C and 5D, even when the tissue fastener 10 is placed in the tissue, the basic loop L1 of the first and second tissue fixing sections 11 and 12 can stabilize a shape of the tissue fastener 10 without causing imperfect alignment.

In the end 14B corresponding to a coupling portion of the spring portion 14 with the end coil portion 15, the metal wire changes the angle at which it is extended. The end coil portion 15 is formed in a bent state so as to form a loop perpendicular to the central axis of the basic loop L1. Thus, the loop of the end coil portion 15 has a shape parallel to the basic loop L1.

As shown in FIG. 3, an end 15A of the end coil portion 15 is provided with a coupling portion 16 for coupling to a stylet 60 as described below.

As shown in FIGS. 3 and 4A, the coupling portion 16 is formed in an approximately cylindrical shape extending on the same axis as the metal wire configuring the tissue fastener 10. The opposite side of the end of the coupling portion 16 to which the metal wire is connected is formed in a shape in which it is cut into halves along an axial cross section. In greater detail, the coupling portion 16 includes an end face 16A and a through hole 16B. The end face 16A is formed so as to have the central axis of the cylindrical shape and to be directed toward the radial outer side of the basic loop L1. The through hole 16B is formed in such a way that one end thereof opens to the end face 16A and extends from the end face 16A in a direction orthogonal to the end face 16A.

The loop formed by the end coil portion 15 has a greater diameter than that formed by the spring portion 14. Thus, as shown in FIG. 4A in the plan view, when the tissue fastener 10 is viewed from the central axis direction of the basic loop L1, the basic loop L1 is at the innermost side. A second loop L2 formed by the spring portion 14 is located outside the basic loop L1. A third loop L3 formed by the end coil portion 15 is located outside the second loop L2. The basic loop L1, the second loop L2, and the third loop L3 do not overlap with one another in the radial direction of the basic loop L1.

Hereinafter, the applicator 20 of the implant placement device 1 will be described.

As shown in FIG. 2A, the applicator 20 is an instrument for placing the tissue fastener 10 in the body using an endoscope. The applicator 20 at least includes a tubular member (long shaft member) 50, a stylet 60, a sheath 70, a sheath operating part 100, and a notch (contact part) 71C. The applicator 20 includes an insertion part 30 and a main body 40. Further, the applicator 20 may include a mounting part 21. The mounting part 21 fixes the applicator 20 to, for instance, a forceps channel (treatment tool channel) 7 of the endoscope 2 shown in FIG. 6. The insertion part 30 is inserted into the forceps channel 7 of the endoscope 2, and guides the tissue fastener 10 up to target living tissue. The main body 40 is provided at the side of a proximal end of an insertion direction of the insertion part 30, and performs an operation of placing the tissue fastener 10.

As shown in FIGS. 2A and 6, the mounting part 21 includes a luer lock connector 22 and a coupling support 23 (see FIG. 6). The luer lock connector 22 is screwed on the port 8 of the forceps channel 7. The coupling support 23 couples the endoscope 2 and the applicator 20.

As shown in FIG. 6, the coupling support 23 includes a frictional engaging portion 24, a slip-out stopper pin 25, and a stopper portion 26. The frictional engaging portion 24 is formed in a tube shape so as to cause the operating part 3 of the endoscope 2 to be plugged in and to be frictionally engaged with an outer surface of the operating part 3. The slip-out stopper pin 25 pierces an outer peripheral portion of the port 8 such that the frictional engaging portion 24 does not come out of the operating part 3. The stopper portion 26 inserts and screws a tubular sheath slider 104 to be described below. In this way, the applicator 20 and the endoscope 2 are fixed via the coupling support 23 fixed to the applicator 20. Thereby, when the applicator 20 is mounted on the endoscope 2 by the coupling support 23, the applicator 20 can be supported so as not to be separated from the mouthpiece 8 of the forceps channel 7 even when a user does not support the applicator 20.

As shown in FIG. 2A, the insertion part 30 includes the tubular member (long shaft member) 50, the stylet 60, and the sheath 70. The tubular member 50 includes a lumen running along a longitudinal axis of the tubular member 50 such that the tissue fastener 10 is disposed in a stretched state, and an opening formed so as to communicate with the lumen. The stylet 60 is installed in the lumen so as to be movable in the lumen in the longitudinal axis of the tubular member 50 in order to push the tissue fastener 10 out of the tubular member 50. The stylet 60 is inserted into and disposed in the tubular member 50. The sheath 70 has the shape of a pipe which is installed so as to be rotatable around the longitudinal axis of the tubular member 50 and into which the tubular member 50 is inserted. The sheath 70 houses the tubular member 50 and the stylet 60. All of the tubular member 50, the stylet 60, and the sheath 70 have flexibility and are coaxially disposed. The insertion part 30 is formed so as to have an axial length longer than that of the aforementioned forceps channel 7.

The tubular member 50 is used to house the tissue fastener 10 in a stretched state. A material of the tubular member 50 has such a hardness that the tubular member 50 is not bent when the tubular member 50 is inserted into the living tissue. Further, the material of the tubular member 50 may have such flexibility as to be able to be bent along the course of the forceps channel 7 when the tubular member 50 is inserted into the forceps channel 7 of the endoscope 2. As the material of the tubular member 50, for example, stainless steel or a superelastic alloy represented by a nickel titanium alloy (NiTi) may be employed.

The tubular member 50 is inserted into the living tissue from the side of a distal end 51 thereof. The distal end 51 of the tubular member 50 includes an inclined end face 51A formed so as to be inclined with respect to the longitudinal direction of the tubular member 50. Thereby, the distal end of the tubular member 50 is sharply finished. Further, the tubular member 50 is slightly bent at a part of the tubular member 50 which is located at the side of the distal end 51 thereof so that a proximal end of the inclined end face 51A is directed toward a bent interior.

Further, the distal end 51 of the tubular member 50 is provided with an electrode, and electric current is caused to flow to the distal end 51 and to cauterize and cut the living tissue. Thereby, the tubular member 50 may be configured so as to be inserted into the living tissue. In this case, the distal end 51 of the tubular member 50 may not be sharply formed.

The stylet 60 is disposed inside the tubular member 50 so as to be closer to the proximal end than the tissue fastener 10. The stylet 60 is formed in the shape of a rod that can move forward/backward in the tubular member 50. A coupling portion 63 coupled to the aforementioned coupling portion 16 provided for the tissue fastener 10 is fixed to a distal end 61 of the stylet 60.

As shown in FIGS. 7A and 7B, the coupling portion 63 includes an end face 63A and a projection 63B. The end face 63A is formed so as to be in contact with the end face 16A of the coupling portion 16. The projection 63B is inserted into the through hole 16B of the coupling portion 16.

The end face 63A is positioned such that a circumferential position relative to the tubular member 50 is directed toward the proximal end 51B of the inclined end face 51A formed at the distal end 51 of the tubular member 50 (see FIG. 2A).

When the tissue fastener 10 is housed inside the tubular member 50, the projection 63B is inserted into the through hole 16B. The end face 16A and the end face 63A are in contact with each other. For this reason, the tissue fastener 10 can move forward/backward in the tubular member 50 along with the stylet 60. When the stylet 60 is rotated around an axis, the stylet 60 and the tissue fastener 10 are rotated together. In the tubular member 50, even if the end face 16A and the end face 63A move to different directions separately, when the coupling portion 16 and the coupling portion 63 are combined, the projection 63B can not be pulled out of the through hole 16B. For this reason, the tissue fastener 10 and the stylet 60 are not disengaged inside the tubular member 50.

A three-layer coil sheath 53 wound around the outer surface of the tubular member 50 in three layers is provided between the tubular member 50 and the sheath 70. As a material of the three-layer coil sheath 53, for example, a wire made of a metal may be employed. This wire may be wound to form a coil sheath having a three-layer structure. Further, the three-layer coil sheath 53 is fixed to the tubular member 50, but not to the sheath 70.

The sheath 70 is a tubular member which has flexibility and into which the tubular member 50 is inserted. The sheath 70 has a linear shape in a state in which no external force is applied. The tubular member 50 bent slightly is inserted, and thereby a part of the sheath 70 which is located at the side of a distal end 71 is slightly bent. Further, the distal end 71 of the sheath 70 includes a flat face 71A, a chamfer 71B, and a notch (contact part) 71C. The flat face 71A is formed flat so as to be orthogonal to a longitudinal direction of the sheath 70. The chamfer 71B is formed in a shape in which an edge of an outer circumferential portion of the flat face 71A is removed so as to easily insert the sheath 70 into the forceps channel 7 of the endoscope 2. The notch 71C is provided for the distal end of the sheath 70 in order to rotate the tissue fastener 10 in response to manipulation of the sheath operating part 100. The notch 71C has a contact surface that is in contact with a part of the tissue fastener 10, which is pushed out of the opening of the tubular member 50 by the stylet 60, in a rotational direction around the longitudinal axis of the tubular member 50 in a state in which the opening of the tubular member 50 is located inside the sheath 70. In the present embodiment, the notch 71C has a shape in which a part of the outer circumferential surface of the sheath 70 is cut off in the longitudinal direction of the sheath 70.

The notch 71C has a gap into which the metal wire configuring the tissue fastener 10 can be at least partly inserted at the distal end of the sheath 70. Further, the notch 71C has a gap greater than a diameter of the metal wire configuring the tissue fastener 10 at the distal end of the sheath 70. In addition, as shown in FIG. 2C, as a result of the part of the outer circumferential surface of the sheath 70 being cut off, a shape in which one projection extending in the central axis direction of the sheath 70 seems to be formed at the distal end of the sheath 70 is also included in the notch 71C referred to in the present embodiment.

When measured from the distal end of the sheath 70 along the central axis of the sheath 70, a length dimension of the notch 71C may be greater than a radius of the metal wire configuring the tissue fastener 10. Furthermore, the length dimension of the notch 71C may be greater than the diameter of the metal wire configuring the tissue fastener 10. In the notch 71C, a pair of opposite surfaces (contact surfaces) 71Ca and 71Cb directed in a circumferential direction of the sheath 70 are surfaces that are in contact with the metal wire configuring the tissue fastener 10 in order to cause the tissue fastener 10 to be rotated around the central axis of the sheath 70 using the sheath 70.

A bent surface may be formed on the pair of opposite surfaces 71Ca and 71Cb in part or in whole. Furthermore, it is not necessary for the opposite surface 71Ca and the opposite surface 71Cb to be diagonally opposite to each other. In the present embodiment, the pair of opposite surfaces 71Ca and 71Cb are surfaces parallel to each other.

As shown in FIG. 2A, the main body 40 includes an operating body 41 formed in an approximately tubular shape. The operating body 41 is provided with a tubular member operating part 80, a stylet operating part 90, a sheath operating part (operating part) 100, and a rotation interlocking mechanism 110. The tubular member operating part 80 operates the tubular member 50. The stylet operating part 90 operates the stylet 60. The sheath operating part 100 is provided at the side of the proximal end of the sheath 70 and can operate the sheath 70 so as to be rotated around the longitudinal axis of the tubular member 50. The sheath operating part 100 operates the sheath 70. The rotation interlocking mechanism 110 couples the tubular member operating part 80, the stylet operating part 90, and the sheath operating part 100, and interlocks respective rotational motions.

The operating body 41 is provided with a long hole 42 (see FIG. 1), a guide groove 43 (see FIG. 1), and a regulating groove 44 (see FIG. 2A), each of which extends in the longitudinal direction of the operating body 41. A coupling screw 81C of the tubular member operating part 80 which will be described below passes through the long hole 42. A positioning screw 89 to be described below is fitted into the guide groove 43. A regulating member 86 to be described below is fitted into the regulating groove 44.

As shown in FIGS. 2A and 8, the tubular member operating part 80 includes a fixing portion 81, a tubular cam tube 82, a tubular member slider 84, and a substantially tubular slide stopper 87. The fixing portion 81 is fixed to the proximal end 52 of the tubular member 50. The tubular cam tube 82 is formed in a tubular shape and is coupled to the fixing portion 81. The tubular member slider 84 is coupled to the fixing portion 81. The slide stopper 87 is formed in a tubular shape and is fitted into an outer circumferential surface of the operating body 41 so as to be closer to the distal end 41A of the operating body 41 than the tubular member slider 84.

The fixing portion 81 includes a fixing member 81A and a tubular supporting member 81B. The fixing member 81A is formed in an approximate disc shape, and the tubular member 50 is fixed to the fixing member 81A. The tubular supporting member 81B is formed in a tubular shape and is coupled with the fixing member 81A partly rotatable around the central axis of the fixing member 81A. The tubular supporting member 81B is formed along an inner wall of the operating body 41 in the operating body 41. The tubular supporting member 81B is partly movable in the operating body 41 in the longitudinal direction of the operating body 41. The tubular supporting member 81B has a circumferential position positioned relative to the operating body 41.

The coupling screw 81C is detachably installed at a side of a proximal end of the fixing portion 81. As shown in FIG. 8, the coupling screw 81C is screwed from an outer side of the operating body 41 via the long hole 42 into a radial inner side of the operating body 41. Further, as shown in FIG. 2A, the coupling screw 81C passes through the tubular supporting member 81B and the cam tube 82. In a state in which the coupling screw 81C is mounted, the fixing portion 81 and the tubular cam tube 82 are fixed. For this reason, the fixing portion 81 and the tubular cam tube 82 can move together relative to the operating body 41 within the range of a longitudinal length of the long hole 42.

As shown in FIG. 2A, the tubular cam tube 82 is a member that causes the stylet 60 to be rotated around an axis of the stylet 60 and causes the stylet 60 to partly move in the axial direction of the tubular member 50. An outer wall part of the tubular cam tube 82 is provided with a spiral cam 83 formed so as to cut off a part thereof.

The spiral cam 83 includes a first spiral cam 83A and a second spiral cam 83B. The first spiral cam 83A is located at the side of a distal end 82A of the tubular cam tube 82. The second spiral cam 83B is located closer to a proximal end 82B than the first spiral cam 83A.

The first spiral cam 83A is engaged with the tubular supporting member 81B. To be more specific, a pin 81D provided at a radial inner side in the tubular supporting member 81B in a protruding fashion is stuck in the first spiral cam 83A. The first spiral cam 83A has a helical shape that travels around an axis of the tubular cam tube 82 in a rightward direction with the approach from the side of a proximal end 82B to the side of a distal end 82A of the tubular cam tube 82 when viewed from the side of the distal end 82A to the side of the proximal end 82B of the tubular cam tube 82.

As shown in FIGS. 2A and 9, the second spiral cam 83B has a helical shape of the same direction as the spiral cam 83A. Furthermore, a shape of the second spiral cam 83B is determined based on the shape of the tissue fastener 10. That is, the second spiral cam 83B usually has the number of turns equal to or more than that of the metal wire in the tissue fastener 10. Furthermore, a length of a lead of the second spiral cam 83B is set to be equal to a length of the metal wire which corresponds to one round in the circumferential direction of the tissue fastener 10. In the present embodiment, the loop of the tissue fastener 10 is configured so that the loop diameter differs in the basic loop (first loop) L1, the second loop L2, and the third loop L3 as described above, and the length of the metal wire differs in the loops. For this reason, the second spiral cam 83B of the present embodiment is formed by changing the length of the lead so as to have the order of the third loop, the second loop, and the first loop from the side of the distal end 82A of the tubular cam tube 82.

As shown in FIGS. 2A and 8, the tubular member slider 84 includes a pair of hooks 85 and a regulating member 86. The pair of hooks 85 couple the tubular member slider 84 to the slide stopper 87. The regulating member 86 is fitted into the regulating groove 44 of the operating body 41.

The pair of hooks 85 are provided on an outer surface of the tubular member slider 84 at positions facing each other in a radial direction. Further, the pair of hooks 85 are respectively biased by, for instance, a flat spring 85C such that a distal end 85A of the hooks 85 is directed to a radial inner side of the tubular member slider 84. A proximal end 85B of the hooks 85 is a portion operated by a user. The proximal end 85B is respectively grasped by, for instance, a thumb and a forefinger of the user, and thereby the distal end 85A of the pair of hooks 85 can be displaced to the radial outer side of the tubular member slider 84 at the same time.

As shown in FIG. 8, the slide stopper 87 includes an engaging portion 88 used to engage the distal ends 85A of the hooks 85. The engaging portion 88 includes a taper portion 88A and an engaging groove 88B. The taper portion 88A is inclined so as to be directed to the radial outer side with the approach from a proximal end 87B to a distal end 87A of the slide stopper 87. The engaging groove 88B is formed closer to the distal end 87A than the taper portion 88A so as to be recessed at the radial inner side.

When the hooks 85 of the tubular member slider 84 are engaged with the engaging groove 88B of the slide stopper 87, the slide stopper 87 and the tubular member slider 84 are configured so as not to relatively move in the axial direction.

Furthermore, the slide stopper 87 is mounted with a positioning screw 89 having a distal end 89A that can be in contact with the outer surface of the operating body 41. The positioning screw 89 is screwed in an inward direction of the slide stopper 87, and thereby the positioning screw 89 comes into contact with the bottom of the guide groove 43 and is pressed to the radial inner side. As a result, the position of the slide stopper 87 relative to the operating body 41 can be fixed.

As shown in FIGS. 2A and 9, the stylet operating part 90 includes a sheath tube 91, a rotation input portion 93, and a fixing portion 94. The sheath tube 91 covers an outer circumference of the tubular cam tube 82. The rotation input portion 93 is fixed to a distal end of the sheath tube 91. The fixing portion 94 is disposed inside the tubular cam tube 82. A proximal end 62 of the stylet 60 is fixed to the fixing portion 94. Further, a rotation regulating portion 97, which regulates a circumferential rotational motion of the tubular member slider 84 relative to the sheath tube 91, is provided between the distal end of the sheath tube 91 and the tubular member slider 84.

As shown in FIG. 9, the sheath tube 91 is provided with a long hole 92 in an outer wall thereof which is formed by extending in a longitudinal direction of the sheath tube 91. The long hole 92 includes a long hole 92A and a long hole 92B. As shown in FIGS. 2A and 9, the long hole 92A is located at the side of a distal end 91A of the sheath tube 91. The long hole 92B is located at the side of a proximal end 91B of the sheath tube 91. When the longitudinal direction of the sheath tube 91 is defined as a longitudinal direction of the long hole 92, widths of the long hole 92A and the long hole 92B are different from each other. The width of the long hole 92A is formed so as to be narrower than that of the long hole 92B.

The rotation input portion 93 is a portion which a user grasps to rotate the sheath tube 91. The rotation input portion 93 is provided with a concavo-convex portion 93A (see FIG. 2A) on an outer surface thereof which prevents the hand of the user from sliding in a circumferential direction when the rotation input portion 93 is grasped by the hand of the user.

As shown in FIGS. 2A, 10A, and 10B, the fixing portion 94 includes a guide pin 95 protruding to a radial outer side of the tubular cam tube 82. The guide pin 95 passes through the spiral cam 83 of the tubular cam tube 82. In addition, the guide pin 95 passes through the long hole 92B of the sheath tube 91. The guide pin 95 includes a first wall portion 95A and a second wall portion 95B. The first wall portion 95A has a narrower width than the long hole 92A. The second wall portion 95B has a width that is wider than the width of the long hole 92A and is narrower than the width of the long hole 92B.

The first wall portion 95A and the second wall portion 95B are disposed around an axis of the guide pin 95 at positions at which they are offset by 90 degrees. For this reason, in a state in which the second wall portion 95B is directed in a widthwise direction of the long hole 92B, the guide pin 95 is caught between the long hole 92A and the long hole 92B. The guide pin 95 is rotated around its axis by 90 degrees, and the first wall portion 95A is directed in the widthwise direction of the long hole 92B. Thereby, the guide pin 95 can go into the long hole 92A.

A protruding end of the guide pin 95 is provided with a projection 96 protruding to a radial outer side of the guide pin 95. The projection 96 can be used as an indicator for a user grasping a position of the first wall portion 95A or the second wall portion 95B when the guide pin 95 is rotated around its axis.

As shown in FIG. 2A, the rotation regulating portion 97 includes a contact part 98 and a rotation regulating screw 99. The contact part 98 is provided at the distal end of the sheath tube 91. The contact part 98 is formed in an annular shape, and an outer surface thereof is partly formed so as to be flat. The rotation regulating screw 99 is screwed on the tubular member slider 84 such that a distal end 99A thereof is in contact with the contact part 98. The rotation regulating screw 99 is detachable from the tubular member slider 84. For this reason, in a state in which the rotation regulating screw 99 is attached, the tubular member slider 84 and the sheath tube 91 are not subjected to relative rotation. In a state in which the rotation regulating screw 99 is detached, the tubular member slider 84 and the sheath tube 91 can be subjected to relative rotation.

As shown in FIGS. 2A and 11, the sheath operating part 100 is provided at the side of the distal end 41A of the operating body 41 of the main body 40. The sheath operating part 100 includes a fixing portion 101, a substantially tubular cam tube 102, and a tubular sheath slider 104. The fixing portion 101 is formed in an approximate disc shape. A proximal end 72 of the sheath 70 is fixed in the center of the fixing portion 101. The cam tube 102 is formed in an approximately cylindrical shape. The cam tube 102 is coupled with the fixing portion 101 so as to be relatively rotatable around the axis of the sheath 70. The tubular sheath slider 104 is formed in a tubular shape. The tubular sheath slider 104 is installed on an outer circumference of the cam tube 102 on the same axis as the cam tube 102.

As shown in FIG. 11, the cam tube 102 includes a tilt cam groove 103. The tilt cam groove 103 has a shape in which a wall part thereof is partly cut off so as to form part of a helix that travels in a rightward direction with the movement from a proximal end 102B to a distal end 102A when viewed from the proximal end 102B toward the distal end 102A. In the present embodiment, in the tilt cam groove 103, a length La measured between both circumferential ends 103A and 103B in an axial direction of the cam tube 102 may be set so as to be shorter than a length of the metal wire which corresponds to one turn of the basic loop L1 of the tissue fastener 10.

As shown in FIG. 12, the tubular sheath slider 104 includes a first cam groove 105 and a second cam groove 106. The cam groove 105 extends in the longitudinal direction of the main body 40. The cam groove 106 extends in a circumferential direction of the tubular sheath slider 104. The cam groove 105 and the cam groove 106 are formed by connection.

An elastic stopper 107 having a projection 107A projecting to a widthwise inner side of the cam groove 105 is provided at an end 105A of the cam groove 105 which is located at the side of a distal end 104A of the tubular sheath slider 104. An elastic stopper 108 having a projection 108A projecting to a widthwise inner side of the cam groove 106 is provided at an end of the cam groove 106 which is located at a side distant from cam groove 105 in the circumferential direction of the tubular sheath slider 104. The elastic stoppers 107 and 108 are formed with escape parts 107B and 108B that escape when the projections 107A and 108A move to the widthwise outer sides of the cam grooves 105 and 106, respectively.

As shown in FIGS. 11 and 12, the sheath operating part 100 is provided with a sheath stopper 109. The sheath stopper 109 is screwed on the operating body 41 so as to pass through the cam grooves 105 and 106 of the tubular sheath slider 104 and the tilt cam groove 103 of the cam tube 102. The sheath stopper 109 includes a threaded portion 109A and a large-diameter part 109B formed in a larger diameter than the threaded portion 109A. The sheath stopper 109 is screwed onto the operating body 41, and thereby the cam tube 102 and the tubular sheath slider 104 are pressed against and fixed to the operating body 41 by the large-diameter part 109B.

As shown in FIGS. 2A and 13, the rotation interlocking mechanism 110 includes shaft members 111, 112, and 113 that are provided by extending in the longitudinal direction of the main body 40. The shaft members 111, 112, and 113 are inserted into both the fixing portion 81 of the tubular member operating part 80 and the fixing portion 94 of the stylet operating part 90. The shaft members 111, 112, and 113 are fixed to the fixing portion 101 of the sheath operating part 100. A holding portion 114, which holds the shaft members 111, 112, and 113 in a predetermined positional relation, is fixed to the shaft members 111, 112, and 113. In the present embodiment, the shaft members 111, 112, and 113 are disposed at a position that is equidistant from a longitudinal axis of the main body 40 in a radial direction (see FIG. 10B). In other words, the longitudinal axis of the main body 40 is a central axis of the tubular member 50 and the stylet 60 in the main body 40. The fixing portion 81, the fixing portion 94, and the fixing portion 101 are rotated together by the rotation interlocking mechanism 110. That is, in the present embodiment, the tubular member 50 fixed to the fixing portion 81, the stylet 60 fixed to the fixing portion 94, and the sheath 70 fixed to the fixing portion 101 are rotated together.

When the implant placement device 1 of the present embodiment which has the configuration described above is used, its motion will be described with reference to FIGS. 14 to 35.

Figure 14:
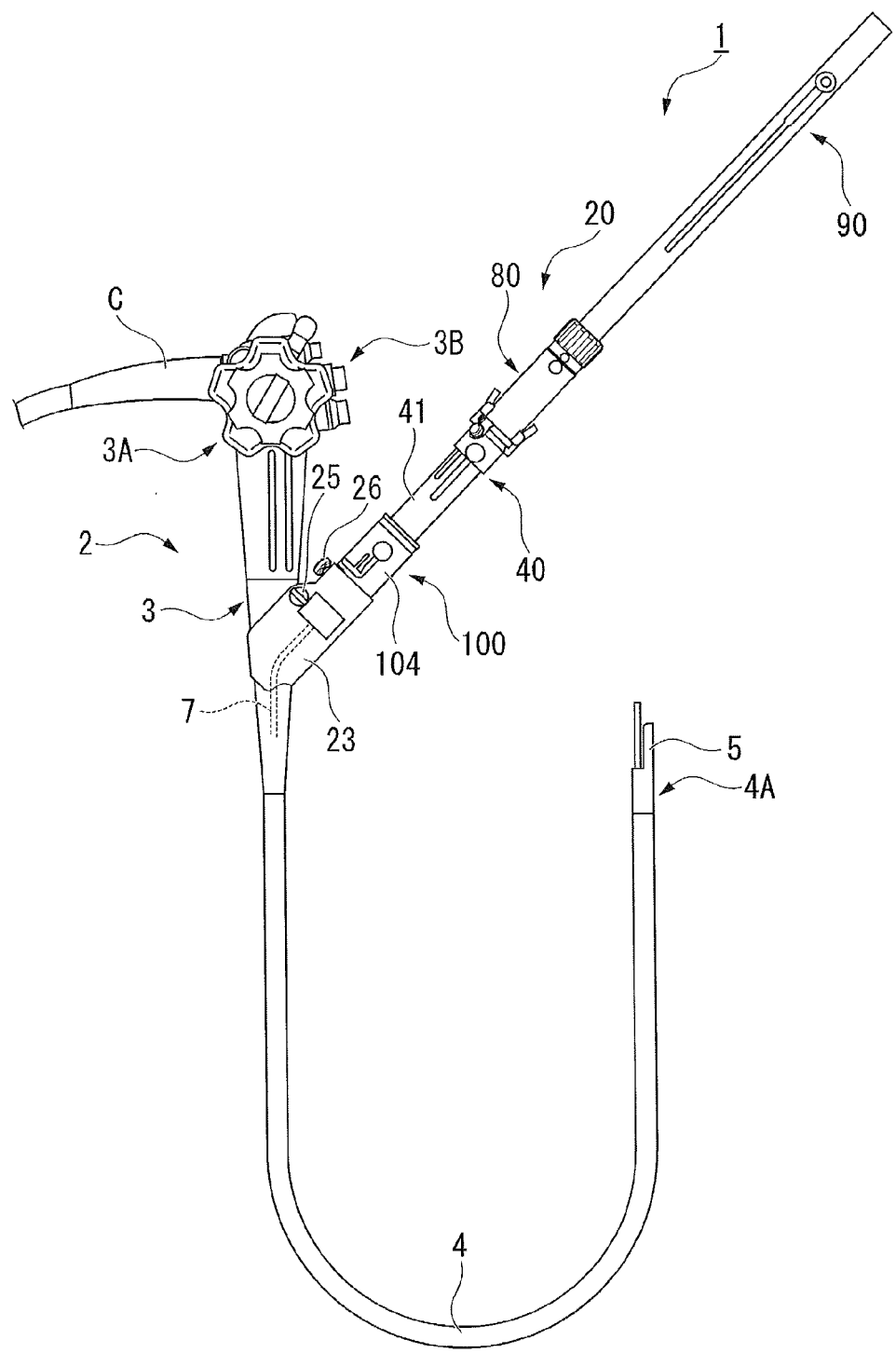
FIG. 14 is a side view showing a state in which the implant placement device according to the embodiment of the present invention and the endoscope are combined.

FIG. 14 is a side view showing a state in which the implant placement device 1 and the endoscope are combined.

In the present embodiment, as shown in FIG. 14, the implant placement device 1 is used along with, for instance, a linear scan type ultrasonic endoscope 2 (hereinafter referred to as an "endoscope 2") having a forceps channel 7.

The endoscope 2 is equipped with a operating part 3, a flexible insertion part 4, a knob 3A, a button 3B, and an ultrasonic observation part 5. The operating part 3 is used outside the body. The insertion part 4 is flexible and extends from the operating part 3. The knob 3A is installed on the operating part 3, and bends a distal end of the insertion part 4. The button 3B performs supply of air and water and suction of air and water. The ultrasonic observation part 5 swells from the distal end 4A of the insertion part 4 to a distal end side. The ultrasonic observation part 5 applies ultrasonic waves from the distal end 4A of the insertion part 4 to the distal end side by an ultrasonic vibrator installed on the distal end 4A of the insertion part 4, and receives reflected waves reflected from, for instance, living tissue. Then, the ultrasonic observation part 5 displays the reflected waves as image information on an external monitor through an interior of the insertion part 4 and an interior of a universal code C of the operating part 3. In this way, the endoscope is configured so as to be able to observe a shape and composition of the living tissue within a range where the ultrasonic waves are applied by the ultrasonic observation part 5.

The endoscope 2 of the present embodiment is a direct-view endoscope. The distal end 4A of the insertion part 4 is provided with an optical observation mechanism (not shown) having a field of vision from the distal end 4A of the insertion part 4 further toward the distal end side. The optical observation mechanism mounts an image capturing lens group and a solid-state image sensing device in the distal end 4A of the insertion part 4, and can be configured so as to show an optical image on the external monitor through the interior of the insertion part 4 and the interior of the universal code C extending from the operating part 3.

Further, the configuration of the endoscope 2 is not limited to a configuration equipped with the ultrasonic observation part 5. The configuration of the endoscope 2 may be a configuration equipped with another probe-type ultrasonic device or a configuration in which observation is made by a means other than the ultrasonic waves. In addition, an endoscope that is not equipped with the ultrasonic observation part 5 may be used. In this case, the interior of a body cavity may be observed using a combination of the endoscope and an apparatus, such as an ultrasonic apparatus, an X-ray apparatus, a magnetic resonance imaging scanner (MRI scanner), or a computed tomography scanner (CT scanner), which is used outside the body.

Figure 15:
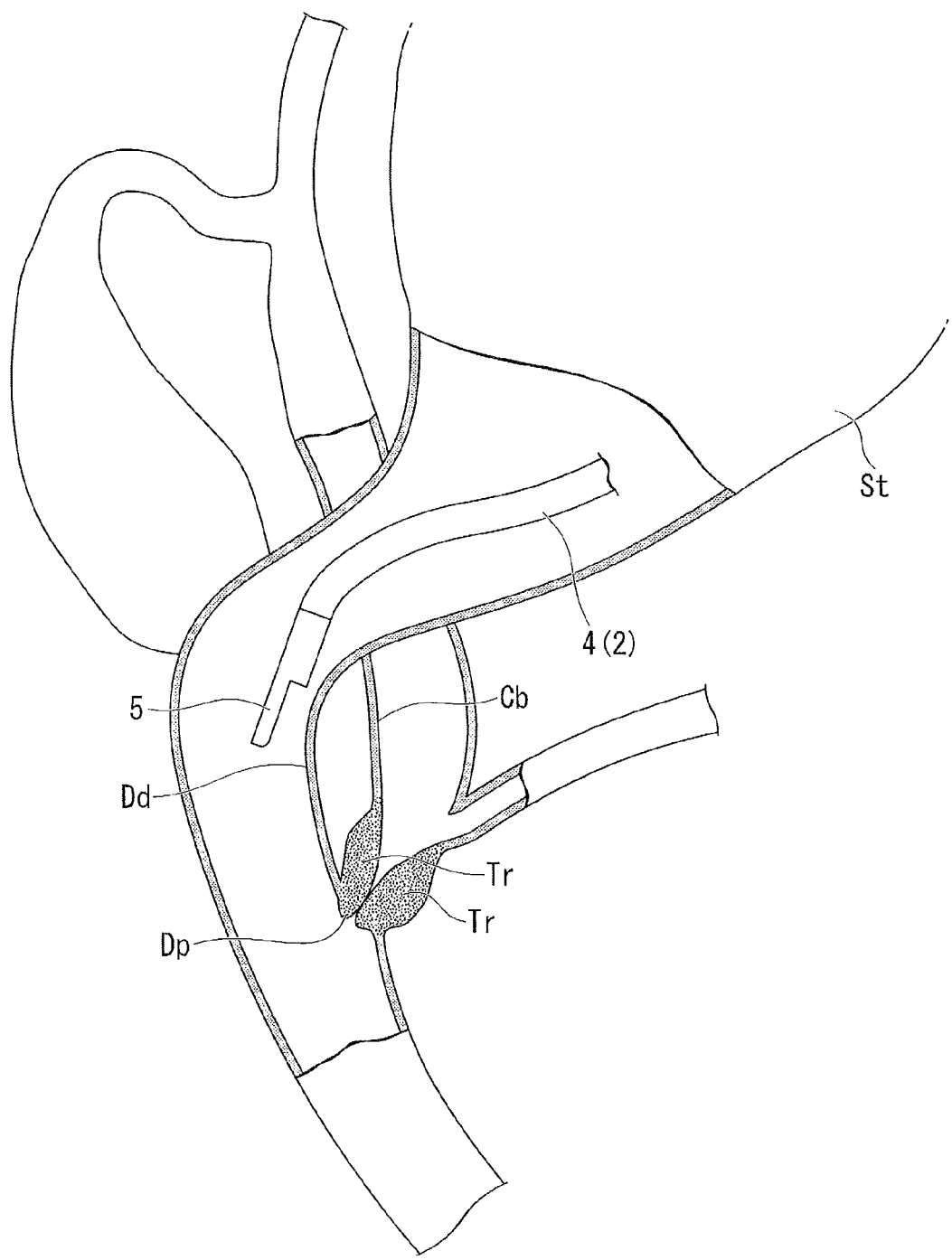
FIG. 15 is a view showing one process of a procedure before the implant placement device according to the embodiment of the present invention is used.

Hereinafter, in a procedure of performing a treatment by combining the implant placement device 1 of the present embodiment into the aforementioned endoscope 2, one example of transduodenal cholangio-drainage will be described taking a procedure of clamping a duodenum and a common bile duct in one body and establishing a through hole to cause the two to communicate with each other by way of example. This procedure is, for instance as shown in FIG. 15, biliary drainage performed when a duodenal papilla Dp is obstructed by a tumor Tr and disables bile from being drained, and the bile dissolves into blood causing jaundice. This procedure allows the bile to be directly drained from a common bile duct Cb to a duodenum Dd.

When the implant placement device 1 of the present embodiment is used, first, the tissue fastener 10 is disposed inside the tubular member 50 in a stretched state. The tubular member 50 is prepared in a position relation in which it is stored in the sheath 70 (see FIG. 2A). Here, as for a position relation of each part in the implant placement device 1, the tubular member 50, the stylet 60, and the sheath 70 are set so as to be located at the most proximal end side within the respective movable ranges (see FIG. 2A). Further, in the state in which only the coupling support 23 is previously fixed to the operating part 3 of the endoscope 2 by the slip-out stopper pin 25 (see FIG. 6), a user begins a procedure.

First, step S1 of inserting the endoscope 2 into the body cavity of a patient and observing a treatment target is performed. FIG. 15 is an explanatory view which shows step S1 and a view showing one process of the procedure before the implant placement device 1 is used. In step S1, as shown in FIG. 15, the insertion part 4 of the endoscope 2 is inserted from the mouth of the patient in a state in which the insertion part 30 of the applicator 20 is not inserted. The endoscope 2 is inserted into the duodenum Dd that is the upper digestive canal. A state of an outer side of the duodenum Dd is examined by the ultrasonic observation part 5, and a user decides a place suitable to establish a through hole adjacent to the common bile duct Cb so as to be closer to a stomach St than the duodenal papilla Dp. Once the place suitable to establish the through hole is decided on, step S1 ends and step S2 begins.

Step S2 is a step of mounting the implant placement device 1 on the endoscope 2. In step S2, a user inserts the insertion part 30 of the applicator 20 shown in FIG. 1 into the forceps channel 7 of the endoscope 2 shown in FIG. 6, and screws and engages the mounting part 21 shown in FIG. 1 on and with the port 8 of the forceps channel 7 shown in FIG. 6. Further, as shown in FIG. 14, the coupling support 23 and the tubular sheath slider 104 are fixed by the stopper portion 26. In this state, even when the user grasps the endoscope 2 without being in contact with the applicator 20, the applicator 20 is not separated from the endoscope 2. As shown in FIG. 14, in the position relation in which the mounting part 21 and the port 8 are engaged, the distal end of the insertion part 30 protrudes from the distal end 4A of the insertion part 4 of the endoscope 2. Once the implant placement device 1 is mounted on the endoscope 2, step S2 ends and step S3 begins.

Figure 16:
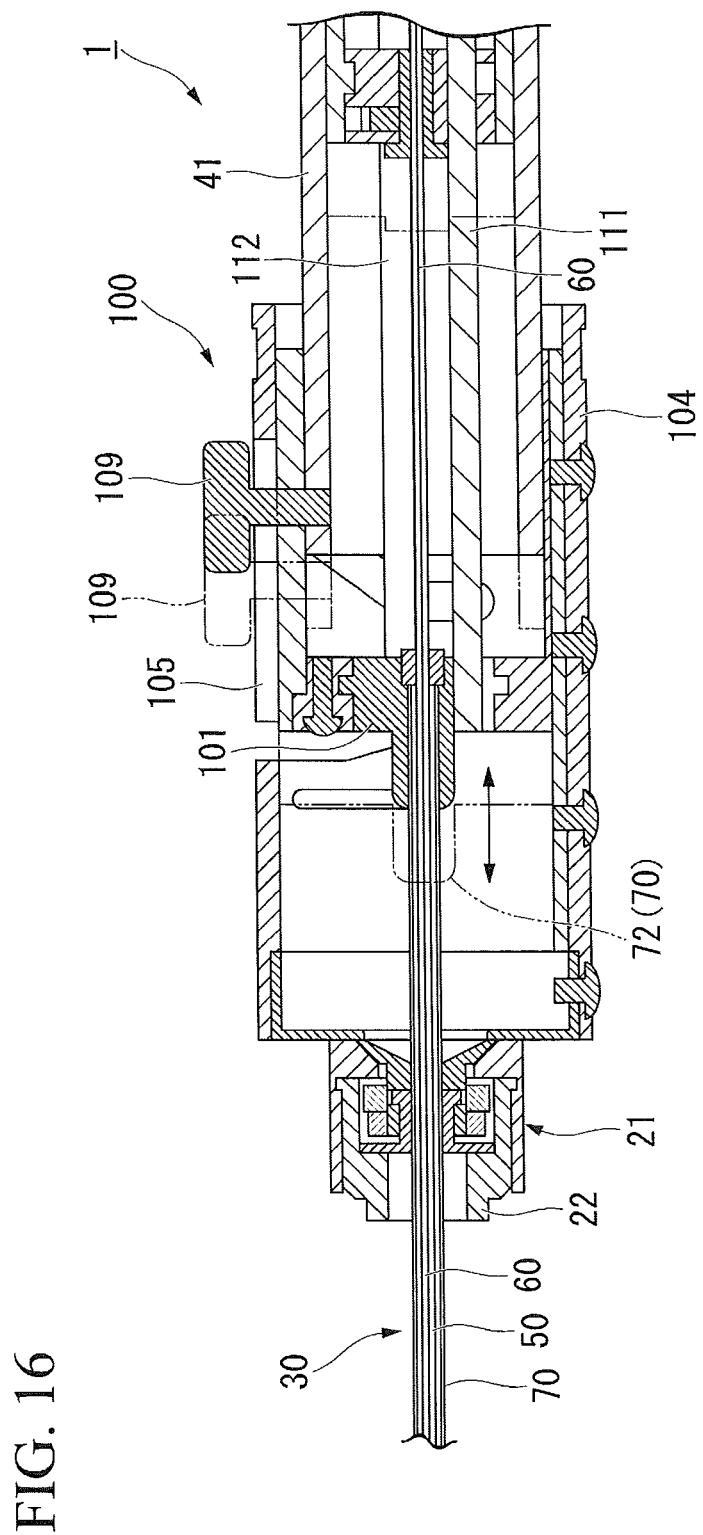
FIG. 16 is a motion explanatory view showing movement of the portion of the sheath operating part when the implant placement device according to the embodiment of the present invention is used.
Figure 17:
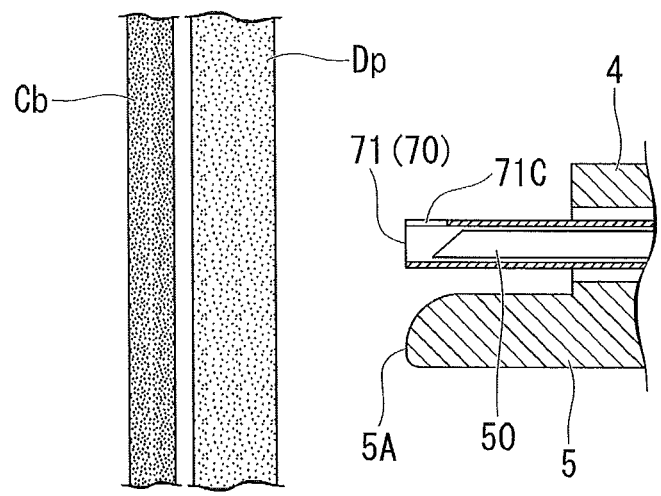
FIG. 17 is a motion explanatory view which shows motion at a distal end side of the insertion part of the endoscope when the implant placement device according to the embodiment of the present invention is used.

Step S3 is a step of adjusting a position of the insertion part 30 with respect to the endoscope 2. FIG. 16 is a motion explanatory view showing movement of a portion of the sheath operating part 100 of the implant placement device 1 in step S3. Further, FIG. 17 is a motion explanatory view which shows motion of step S3 in the distal end side of the insertion part 4 of the endoscope 2 when the implant placement device 1 is used.

In step S3, as shown in FIG. 16, the user loosens the sheath stopper 109 provided for the sheath operating part 100 first. Thereby, the tubular sheath slider 104 and the operating body 41 are relatively movable in the longitudinal direction of the operating body 41. The user causes the operating body 41 to move forward/backward relative to the tubular sheath slider 104, and adjusts the distal end of the sheath 70 so as to be located at a proper predetermined position with respect to the distal end 5A of the ultrasonic observation part 5. In the present embodiment, the aforementioned predetermined position in step S3 refers to a position in which, as shown in FIG. 17, a position of the distal end 5A of the ultrasonic observation part 5 and the distal end 71 of the sheath 70 are identical to each other.

When the operating body 41 is caused to move forward/backward relative to the tubular sheath slider 104, both the tubular member operating part 80 coupled to the operating body 41 and the stylet operating part 90 move forward/backward as one body along with the sheath 70. Thereby, the tubular member 50 and the stylet 60 also move forward/backward as one body. For this reason, a relative position relation of the tubular member 50, the stylet 60, and the sheath 70 remains unchanged. If a position of the insertion part 30 is adjusted to the aforementioned predetermined position, the sheath stopper 109 is fastened to fix the tubular sheath slider 104 and the operating body 41, step S3 ends, and step S4 begins.

Figure 18:
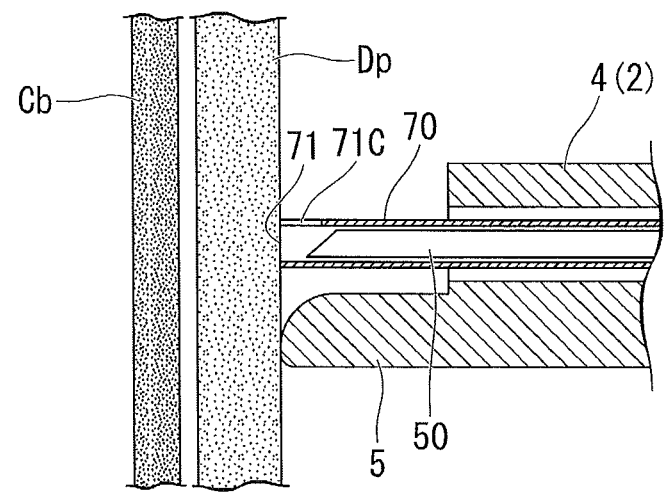
FIG. 18 is a motion explanatory view which shows the movement at the distal end side of the insertion part of the endoscope when the implant placement device according to the embodiment of the present invention is used.

Step S4 is a step of deciding a portion where the tubular member 50 is punctured. FIG. 18 is a motion explanatory view which shows motion at the distal end side of the insertion part 4 of the endoscope 2 when the implant placement device 1 is used.

In step S4, as shown in FIG. 18, the user scans the common bile duct Cb beyond the duodenum Dd using the ultrasonic observation part 5 installed on the endoscope 2, and decides a position at which the tubular member 50 is inserted into the duodenum Dd and the common bile duct Cb. Once a position at which the tubular member 50 is punctured is decided on, step S4 ends and step S5 begins.

Figure 19A:
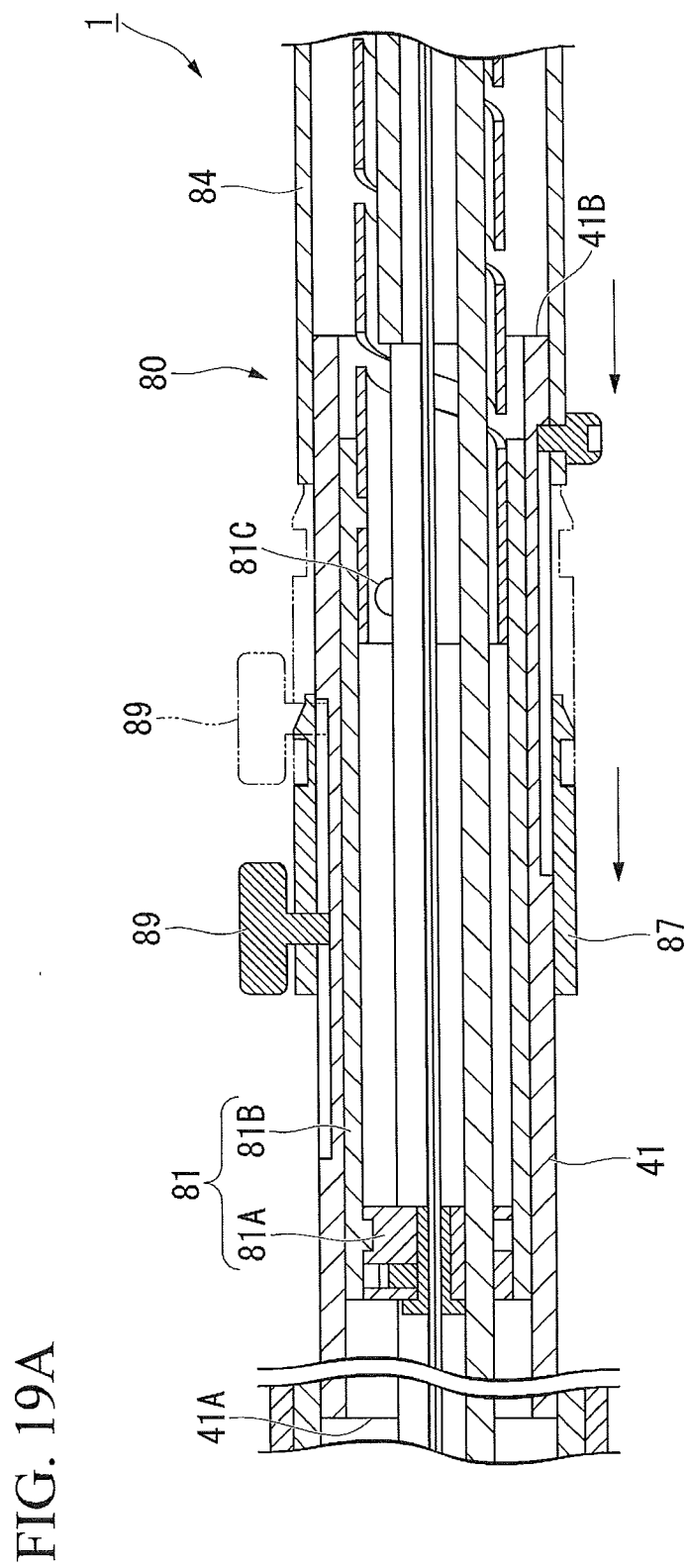
FIG. 19A is a motion explanatory view which shows motion of the tubular member operating part when the implant placement device according to the embodiment of the present invention is used.
Figure 20:
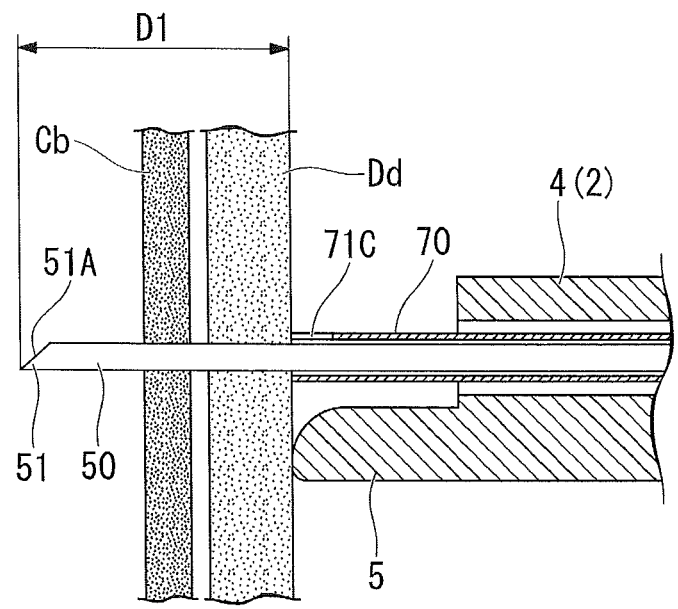
FIG. 20 is a motion explanatory view which shows the movement at the distal end side of the insertion part of the endoscope when the implant placement device according to the embodiment of the present invention is used.

Step S5 is a step of setting a puncturing amount of the tubular member 50 for puncturing the duodenum Dd and the common bile duct Cb. FIGS. 19A and 19B are motion explanatory views which shows motion of the tubular member operating part 80 when the implant placement device 1 is used. FIG. 20 is a motion explanatory view which shows motion at the distal end side of the insertion part 4 of the endoscope 2 when the implant placement device 1 is used.

In step S5, as shown in FIG. 19A, the user loosens the positioning screw 89 mounted on the slide stopper 87 of the tubular member operating part 80 first. Further, as shown in FIG. 19B, the user presses the proximal ends 85B of the pair of hooks 85 mounted on the tubular member slider 84 toward the radial inner side of the tubular member slider 84.

Then, the distal ends 85A of the pair of hooks 85 are separated from the engaging groove 88B of the slide stopper 87, and the tubular member slider 84 and the slide stopper 87 are relatively movable. The slide stopper 87 is movable forward/backward in the longitudinal direction of the operating body 41.

After the user displaces the slide stopper 87 relative to the operating body 41 to a predetermined position, he/she fastens the positioning screw 89 to fix the slide stopper 87 to the operating body 41. In this case, the distance between the slide stopper 87 and the tubular member slider 84 becomes the puncturing amount D1 by which the tubular member 50 is punctured into the living tissue (the duodenum Dd and the common bile duct Cb). Once the puncturing amount by which the tubular member 50 is punctured is set, step S5 ends and step S6 begins.

Step S6 is a step of puncturing the tubular member 50 into the duodenum Dd and the common bile duct Cb. In step S6, as shown in FIG. 19A, the user displaces the tubular member slider 84 relative to the operating body 41 toward the side of the distal end 41A of the operating body 41. Then, as shown in FIG. 2A, the tubular member slider 84 also moves toward the side of the distal end 41A of the operating body 41 along with the fixing portion 81 coupled to the tubular member slider 84 shown in FIG. 19A as one body. Thereby, the tubular member 50 fixed to the fixing portion 81 also moves linearly toward the distal end 51 of the tubular member 50. As shown in FIG. 20, the tubular member 50 is inserted from the distal end 51 into the duodenum Dd and the common bile duct Cb.

The user displaces the tubular member slider 84 relative to the slide stopper 87 until the tubular member slider 84 comes into contact with the slide stopper 87. Then, as shown in FIG. 19B, the distal ends 85A of the pair of hooks 85 installed on the tubular member slider 84 each ride over the taper portion 88A of the slide stopper 87 and are fitted into the engaging groove 88B. Since the slide stopper 87 is fixed to the operating body 41, when the tubular member slider 84 and the slide stopper 87 are engaged, the tubular member slider 84 is also held in a position relation in which it is fixed with respect to the operating body 41. For this reason, the tubular member 50 punctured into the duodenum Dd and the common bile duct Cb does not return to the side of the proximal end 52, and the tubular member 50 is inhibited from coming out of the tissue.

Once the tubular member 50 is punctured into the duodenum Dd and the common bile duct Cb, step S6 ends and step S7 begins.

Figure 21:
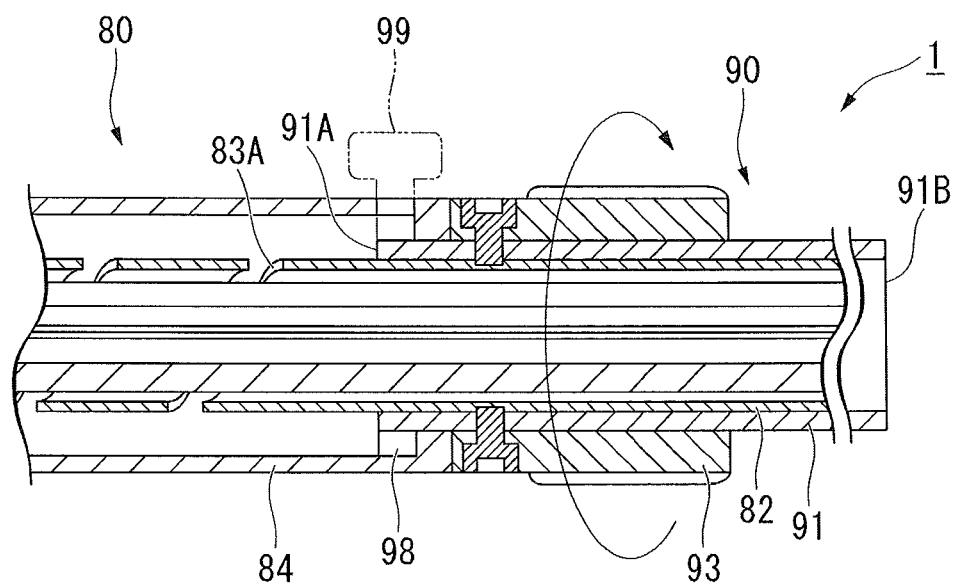
FIG. 21 is a motion explanatory view which shows motion of the stylet operating part when the implant placement device according to the embodiment of the present invention is used.
Figure 22:
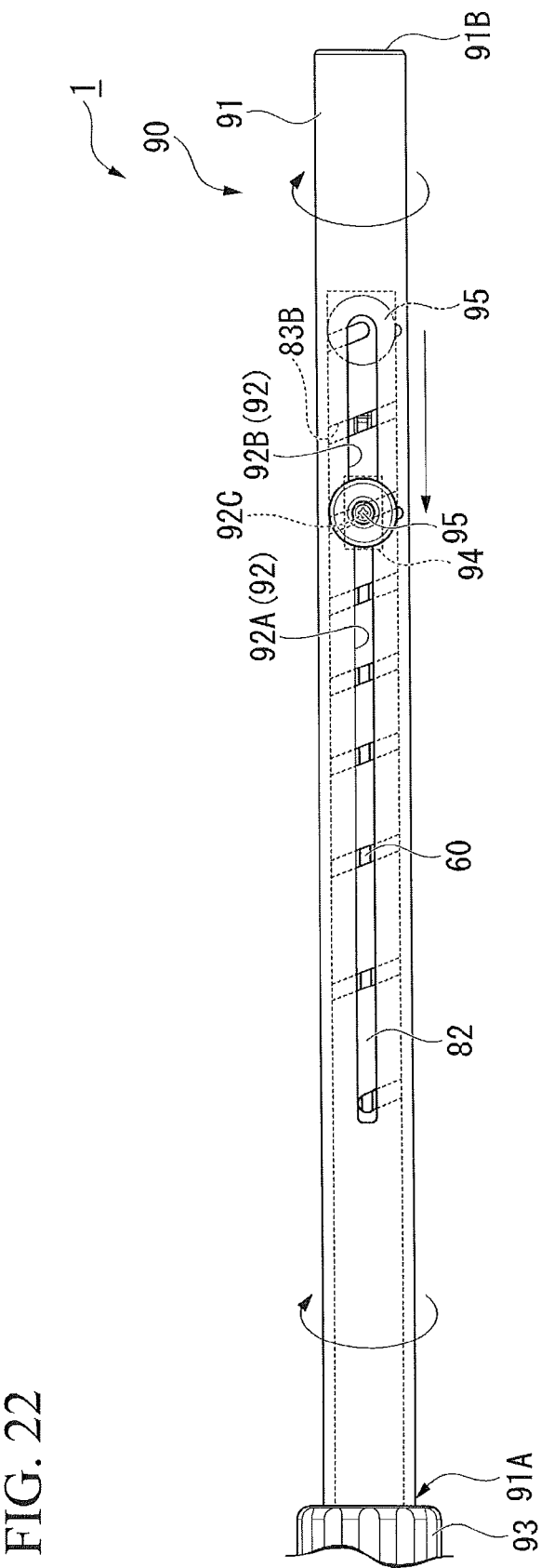
FIG. 22 is a motion explanatory view which shows the movement of the stylet operating part when the implant placement device according to the embodiment of the present invention is used.
Figure 23:
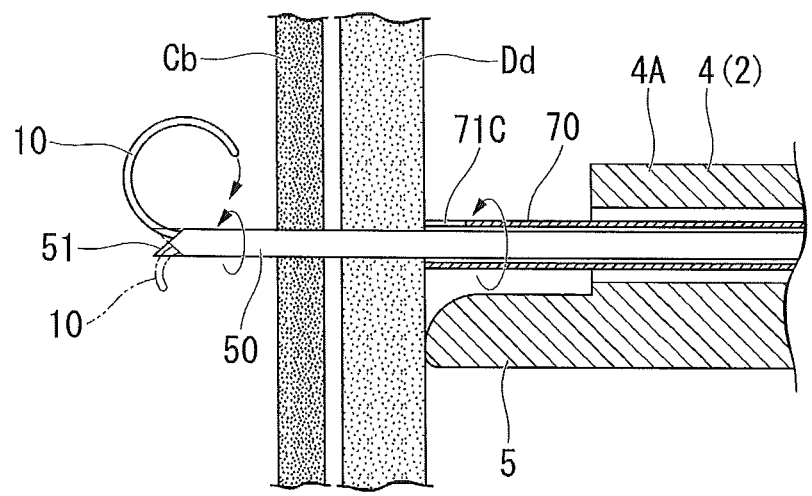
FIG. 23 is a motion explanatory view which shows the movement at the distal end side of the insertion part of the endoscope when the implant placement device according to the embodiment of the present invention is used.

Step S7 is an unreeling process of unreeling the tissue fastener 10 from the tubular member 50 and disposing a part of the tissue fastener 10 at a side of the common bile duct Cb. FIGS. 21 and 22 are motion explanatory views which shows motion of the stylet operating part 90 when the implant placement device 1 is used. FIG. 23 is a motion explanatory view which shows motion at the distal end side of the insertion part 4 of the endoscope 2 when the implant placement device 1 is used.

In step S7, as shown in FIG. 21, the user unfastens the rotation regulating screw 99 attached to the tubular member slider 84. Thereby, the tubular member slider 84 and the sheath tube 91 are disengaged, and the sheath tube 91 and the rotation input portion 93 are allowed to be rotated around the axis relative to the tubular member slider 84.

The user grasps the rotation input portion 93 and rotates the rotation input portion 93 relative to the operating body 41. As shown in FIG. 21 by an arrow, a rotational direction of the rotation input portion 93 is a rightward direction when the sheath tube 91 is viewed from the proximal end 91B toward the distal end 91A. Then, the sheath tube 91 is rotated around its axis relative to the cam tube 82.

As shown in FIGS. 21 and 22, the guide pin 95 is inserted into each of the second spiral cam 83B of the cam tube 82 and the long hole 92 of the sheath tube 91. For this reason, the guide pin 95 moves toward the side of the distal end 91A of the sheath tube 91 along the long hole 92 while being supported on the spiral cam 83. As a result, the fixing portion 94 to which the guide pin 95 is fixed also moves toward the side of the distal end 91A of the sheath tube 91 along with the guide pin 95 as one body. Further, in this case, the sheath tube 91 is rotated around the axis, and thereby the guide pin 95 is also rotated around the same axis as the sheath tube 91.

Due to the fixing portion 94 moving toward the side of the distal end 91A of the sheath tube 91, the stylet 60 moves toward the side of the distal end 51 of the tubular member 50 (see FIG. 2A). Here, since the fixing portion 94 and the stylet 60 are fixed, the stylet 60 is rotated along with the fixing portion 94 in one body.

Here, as shown in FIG. 13, since the fixing portion 81, the fixing portion 94, and the fixing portion 101 are coupled such that rotations thereof are interlocked by the rotation interlocking mechanism 110, the fixing portion 81 and the fixing portion 101 are rotated around the axis together with the fixing portion 94. For this reason, the tubular member 50 fixed to the fixing portion 81 and the sheath 70 fixed to the fixing portion 101 are interlocked with the rotational motion of the stylet 60, and are rotated jointly. As a result, the stylet 60 moves toward the side of the distal end 51 in the tubular member 50 in the axial direction of the tubular member 50 at a circumferential relative position thereof that is the position positioned with the tubular member 50.

At the side of the distal end 4A of the insertion part 4 of the endoscope 2, the tubular member 50 and the stylet 60 are rotated around the axis relative to the operating body 41. For this reason, as shown in FIG. 23, the tissue fastener 10 is rotated around the axis of the tubular member 50 relative to the duodenum Dd and the common bile duct Cb.

As shown in FIG. 22, when the fixing portion 94 moves up to a boundary 92C between the long holes 92A and 92B of the sheath tube 91, the second wall portion 95B of the guide pin 95 is caught in the long hole 92A. Then, the guide pin 95 is engaged with the long hole 92 and the second spiral cam 83B. As such, the user cannot rotate the sheath tube 91. In the present embodiment, the long hole 92A has a length corresponding to two turns of the second spiral cam 83B of the tubular cam tube 82. For this reason, when the sheath tube 91 cannot be rotated, the metal wire of the tissue fastener 10 is unreeled from the distal end 51 of the tubular member 50 by two turns. The tissue fastener 10 is restored to a coil shape at a portion that is unreeled from the distal end 51 of the tubular member 50 by its own superelasticity. Thereby, step S7 ends and step S8 begins.

Figure 24:
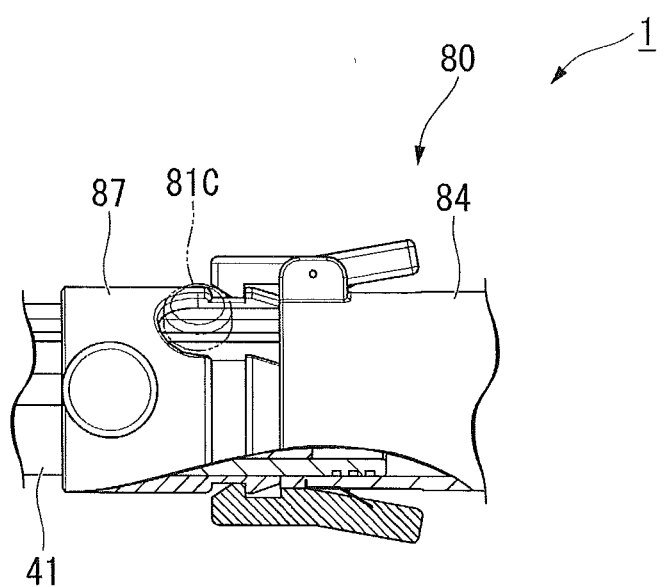
FIG. 24 is a motion explanatory view which shows the movement of the tubular member operating part when the implant placement device according to the embodiment of the present invention is used.
Figure 25:
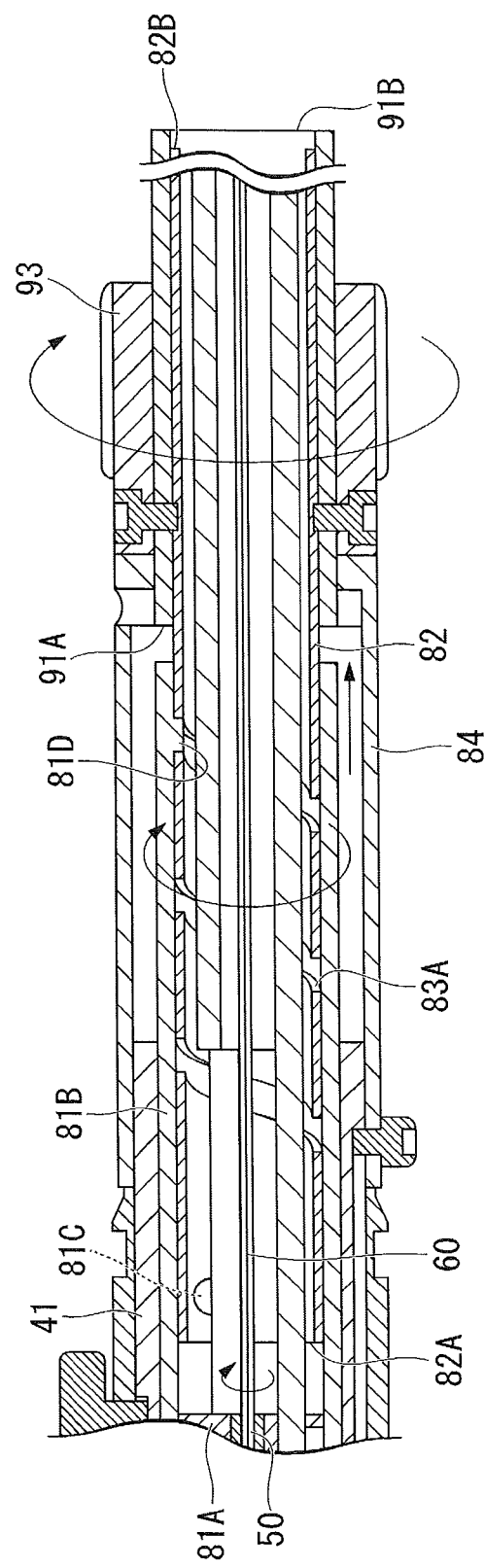
FIG. 25 is a motion explanatory view which shows the movement of the stylet operating part when the implant placement device according to the embodiment of the present invention is used.
Figure 26:
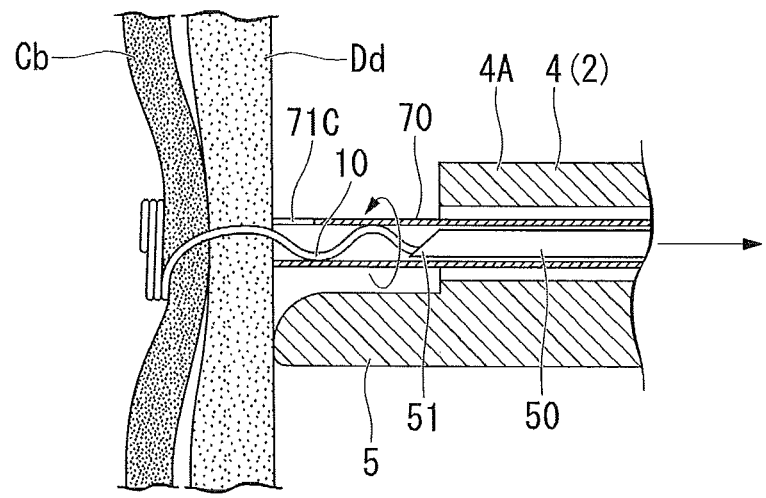
FIG. 26 is a motion explanatory view which shows the movement at the distal end side of the insertion part of the endoscope when the implant placement device according to the embodiment of the present invention is used.

Step S8 is an extracting process of extracting the tubular member 50 from the duodenum Dd and the common bile duct Cb in order to dispose the tissue fastener 10 at the side of the duodenum Dd. FIG. 24 is a motion explanatory view which shows motion of the tubular member operating part 80 when the implant placement device 1 is used. FIG. 25 is a motion explanatory view which shows motion of the stylet operating part 90 when the implant placement device 1 is used. FIG. 26 is a motion explanatory view which shows motion at the distal end side of the insertion part 4 of the endoscope 2 when the implant placement device 1 is used.

In step S8, as shown in FIG. 24, first, the user unfastens the coupling screw 81C attached to the operating body 41 between the tubular member slider 84 and the slide stopper 87. Then, as shown in FIG. 25, the fixture of the fixing portion 81 and the tubular cam tube 82 of the tubular member operating part 80 is released, and the fixing portion 81 and the tubular cam tube 82 are relatively rotatable around the axis. In this state, the user rotates the rotation input portion 93 relative to the operating body 41 in a rightward direction when the sheath tube 91 is viewed from the proximal end 91B to the distal end 91A. Then, the sheath tube 91 and the tubular cam tube 82 undergo no relative rotation because the guide pin 95 is engaged with them, and the tubular cam tube 82 is rotated in the rotational direction of the rotation input portion 93 along with the sheath tube 91.

As the tubular cam tube 82 is rotated, the tubular cam tube 82 and the fixing portion 81 are relatively rotated around the axis. To be more specific, the fixing portion 81 is not rotated relative to the operating body 41, and the tubular cam tube 82 is rotated relative to the operating body 41. The pin 81D installed on the tubular supporting member 81B of the fixing portion 81 slides along the first spiral cam 83A of the tubular cam tube 82. Thereby, the tubular supporting member 81B also moves toward the side of the proximal end 82B of the tubular cam tube 82. Then, the fixing member 81A coupled to the tubular supporting member 81B and the tubular member 50 fixed to the fixing member 81A also move toward the side of the proximal end 82B of the tubular cam tube 82 along with the tubular supporting member 81B. In this case, as shown in FIG. 22, the fixing portion 94 of the stylet operating part 90 is kept fixed by being caught on the boundary 92C between the long hole 92A and the long hole 92B of the sheath tube 91. For this reason, the stylet 60 is rotated around the axis without moving from the position of step S7 in the axial direction. As such, the tubular member 50 and the stylet 60 relatively move such that the tubular member 50 linearly moves toward the side of the proximal end 62 of the stylet 60. As a result, the stylet 60 is pushed to the side of the distal end 51 of the tubular member 50.

At the side of the distal end 4A of the insertion part 4 of the endoscope 2, as shown in FIG. 26, a part of the tissue fastener 10 disposed at the side of the common bile duct Cb is not pulled back to the side of the duodenum Dd by the relative movement of the tubular member 50 and the stylet 60 caused by the linear movement of the aforementioned tubular member 50, and the tubular member 50 is pulled out of the duodenum Dd and the common bile duct Cb, and is drawn into the sheath 70.

Here, the tubular supporting member 81B of the fixing portion 81 is supported on the operating body 41 so as to be movable forward/backward and so as not to be rotatable. For this reason, at a place where the fixing portion 81 moves to the most proximal end side within the movable range inside the operating body 41, the fixing portion 81 can no longer move to the proximal end side of the operating body 41. Thereby, the rotation input portion 93 is not rotated.

The user rotates the rotation input portion 93 shown in FIG. 25 until the rotation input portion 93 is not rotated. When the rotation input portion 93 is not rotated, the movement of pulling out the tubular member 50 is terminated. Thereby, step S8 ends and step S9 begins.

Step S9 is a step of bringing the duodenum Dd and the common bile duct Cb into close contact with each other and causing the endoscope 2 and the duodenum Dd to relatively move so as to be in a positional relation for optically observing the side of the duodenum Dd. That is, step S9 is a pressing process of pressing the duodenum Dd in an inserting direction of the tubular member 50. Up to step S8, the side of the common bile duct Cb is observed via the duodenum Dd by the observation using the ultrasonic observation part 5. In step S9 and later, a treatment of the side of the duodenum Dd is performed by optical observation capable of checking a state in a more intuitive way while observing the side of the duodenum Dd.

Figure 27:
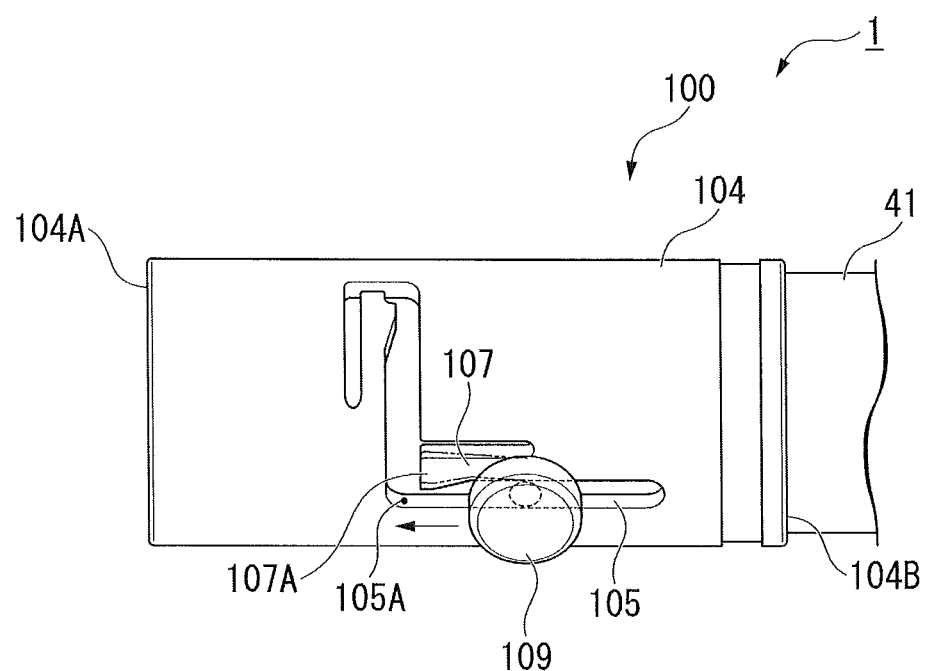
FIG. 27 is a motion explanatory view which shows the movement of the sheath operating part when the implant placement device according to the embodiment of the present invention is used.
Figure 28:
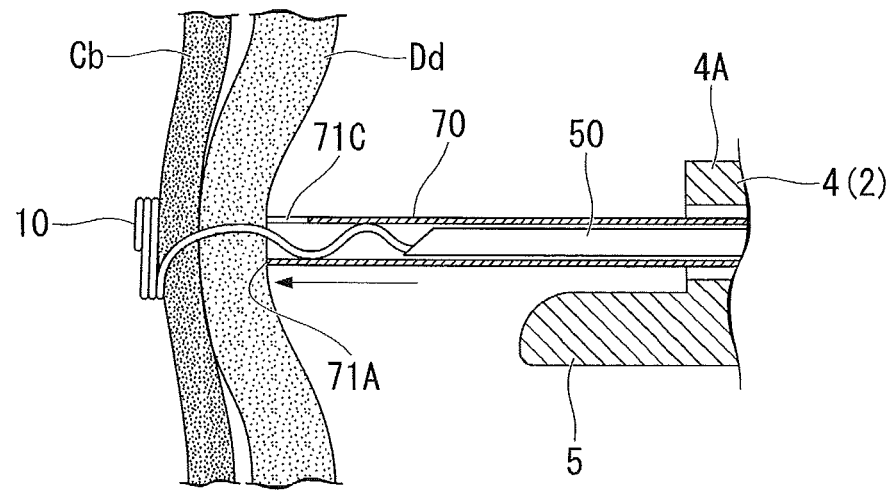
FIG. 28 is a motion explanatory view which shows the movement at the distal end side of the insertion part of the endoscope when the implant placement device according to the embodiment of the present invention is used.

FIG. 27 is a motion explanatory view which shows motion of the sheath operating part 100 when the implant placement device 1 is used. FIG. 28 is a motion explanatory view which shows motion at the distal end side of the insertion part 4 of the endoscope 2 when the implant placement device 1 is used.

In step S9, as shown in FIG. 27, the user again loosens the sheath stopper 109 provided to protrude from the tubular sheath slider 104. Thereby, like the movement in step S3, the tubular member 50, the stylet 60, and the sheath 70 are movable forward/backward relative to the insertion part 4 of the endoscope 2 as one body. The user pushes the operating body 41 in a direction of the distal end 104A of the tubular sheath slider 104. The threaded portion 109A of the sheath stopper 109 passes over the projection 107A, and the sheath stopper 109 reaches the end 105A of the cam groove 105. Then, return of the sheath stopper 109 to the tubular sheath slider 104 is suppressed by the elastic stopper 107.

As shown in FIG. 28, at the side of the distal end 4A of the insertion part 4 of the endoscope 2, the sheath 70 moves so as to be further pushed out to the side of the distal end 71 in contact with the duodenum Dd. For this reason, the duodenum Dd is dented starting from a portion in contact with the sheath 70, and is pressed toward the common bile duct Cb. The duodenum Dd and the common bile duct Cb come into close contact. The sheath 70 is pushed out to the side of the duodenum Dd, and thereby the distal end 4A of the insertion part 4 of the endoscope 2 and the duodenum Dd are separated. Thereby, the endoscope 2 and the duodenum Dd undergo relative movement. A gap through which the duodenum Dd can be observed by the optical observation mechanism installed on the insertion part 4 of the endoscope 2 is formed between the endoscope 2 and the duodenum Dd. Thereby, step S9 ends and step S10 begins.

Figure 29:
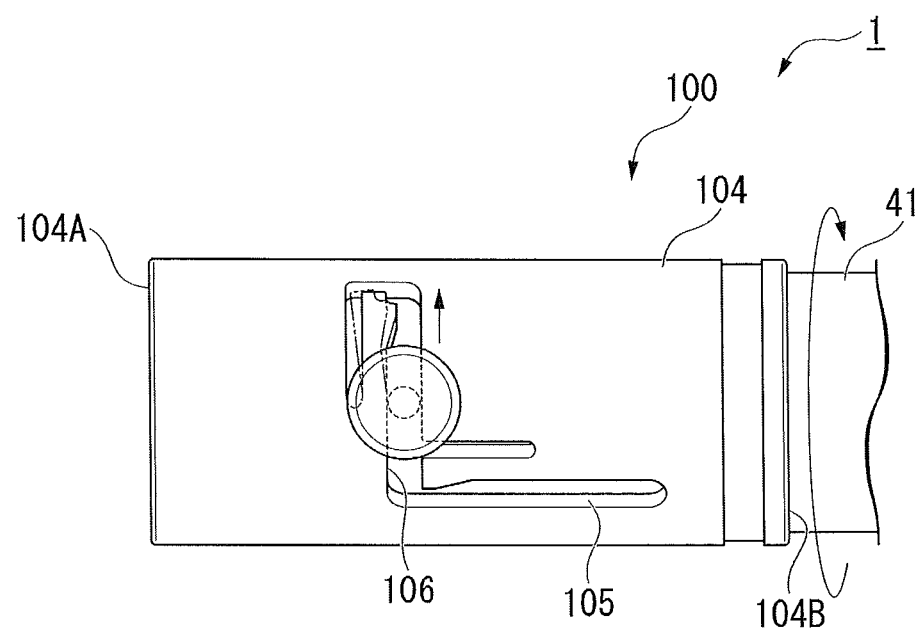
FIG. 29 is a motion explanatory view which shows the movement of the sheath operating part when the implant placement device according to the embodiment of the present invention is used.
Figure 30:
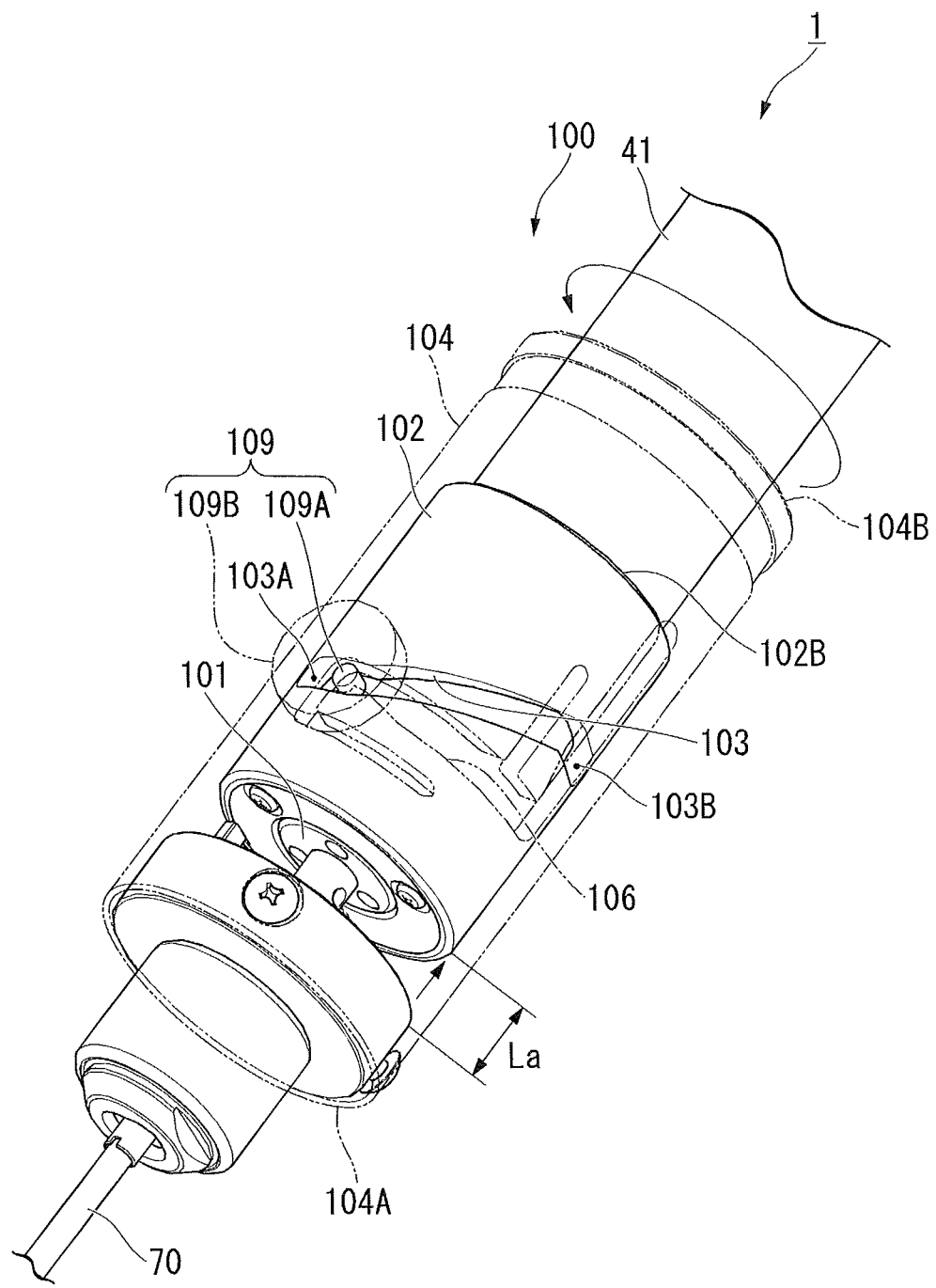
FIG. 30 is a motion explanatory view which shows the movement of the sheath operating part when the implant placement device according to the embodiment of the present invention is used.
Figure 31:
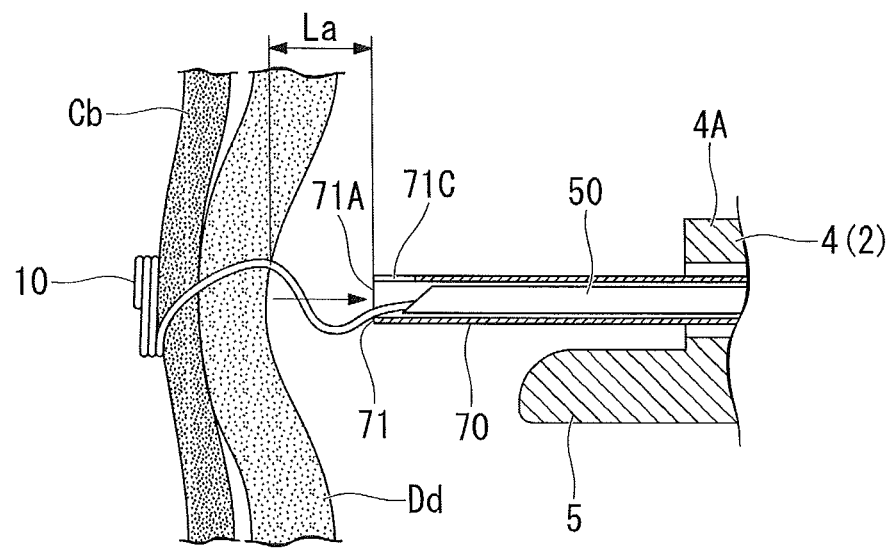
FIG. 31 is a motion explanatory view which shows the movement of the sheath operating part when the implant placement device according to the embodiment of the present invention is used.

Step S10 is an exposing process of exposing the tissue fastener 10 to the side of the duodenum Dd and disposing the tissue fastener 10. FIGS. 29 and 30 are motion explanatory views which shows motion of the sheath operating part 100 when the implant placement device 1 is used. FIG. 31 is a motion explanatory view which shows the movement of the sheath operating part 100 when the implant placement device 1 is used.

In step S10, as shown in FIG. 29, the user relatively rotates the tubular sheath slider 104 and the operating body 41 so as to rotate the operating body 41 relative to the tubular sheath slider 104 in a rightward direction when viewed from the side of the proximal end 104B to the side of the distal end 104A of the tubular sheath slider 104. As shown in FIG. 14, since the tubular sheath slider 104 is fixed to the operating part 3 of the endoscope 2, the operating body 41 is rotated relative to the endoscope 2 and the tubular sheath slider 104. In step S10, the operating body 41 is rotated relative to the endoscope 2 and the tubular sheath slider 104.

Then, as shown in FIG. 30, the sheath stopper 109 moves along the cam groove 106 relative to the tubular sheath slider 104. Simultaneously, the cam tube 102 also relatively moves through the interior of the tilt cam groove 103 of the cam tube 102. Here, the sheath stopper 109 slides on an inner wall portion of the tilt cam groove 103, and also displaces the cam tube 102 to the side of the proximal end 102B by a length La. The cam tube 102 is coupled to the fixing portion 101, and the cam tube 102 and the fixing portion 101 are interlocked with forward/backward movement of the longitudinal direction of the operating body 41. For this reason, the cam tube 102 moves to the side of the proximal end 102B, and thereby the fixing portion 101 and the sheath 70 fixed to the fixing portion 101 move so as to be pulled back to the side of the proximal end 102B of the cam tube 102. In this case, the tubular member 50 and the stylet 60 do not move forward/backward from the position of step S9.

As shown in FIG. 30, the user rotates the operating body 41 relative to the tubular sheath slider 104. Then, the sheath stopper 109 relatively moves along the cam groove 106 up to an end of the cam groove 106 which is distant from the cam groove 105. Here, the sheath stopper 109 rides over the projection 108A of the elastic stopper 108 and moves forward, and return to the side of the cam groove 105 is suppressed by the elastic stopper 108.

As shown in FIG. 22, the sheath tube 91 and the fixing portion 94 are kept fixed by the movement in which the operating body 41 is rotated around the axis relative to tubular sheath slider 104. As such, the fixing portion 94 and the stylet 60 fixed to the fixing portion 94 are rotated around the axis. The rotational motion of the fixing portion 94 is transmitted to each of the tubular member 50 and the sheath 70 by the rotation interlocking mechanism 110. As such, the tubular member 50, the stylet 60, and the sheath 70 are rotated in one body.

As shown in FIG. 31, at the side of the distal end 4A of the insertion part 4 of the endoscope 2, the duodenum Dd is supported by the metal wire of the tissue fastener 10. As such, the aforementioned dented shape is maintained at the duodenum Dd. In the state in which the aforementioned dented shape is maintained at the duodenum Dd, the sheath 70 is pulled back. Thereby, the duodenum Dd and the sheath 70 can be separated by the length La.

The sheath 70 also moves to the side of the proximal end 72 relative to the tubular member 50 and the stylet 60. For this reason, the metal wire of the tissue fastener 10 located inside the sheath 70 relatively moves so as to be unreeled from the distal end 71 of the sheath 70. The tissue fastener 10 unreeled from the distal end 71 of the sheath 70 is sequentially restored from the portion protruding from the sheath 70 in a coil shape by its own superelasticity.

If the metal wire of the tissue fastener 10 is restored in the coil shape, it is important to gradually restore the shape of the metal wire from a portion adjacent to the duodenum Dd. In the present embodiment, a length by which the sheath 70 is pulled back to the side of the proximal end 72 is the length La set by a shape of the tilt cam groove 103. The length La is shorter than a length of one turn of the basic loop L1 of the tissue fastener 10. For this reason, when the sheath 70 is pulled back in step S10, the metal wire of the tissue fastener 10 cannot form a new loop. Instead, the portion, which protrudes from the sheath 70 of the metal wire of the tissue fastener 10, has a curved shape so as to form a part of a loop shape. Further, the tissue fastener 10 can be placed so as to follow the duodenum Dd by integrally rotating the tubular member 50, the stylet 60, and the sheath 70, i.e. the metal wire of the tissue fastener 10 can be inclined to follow the duodenum Dd. Thereby, the curved shape that serves as a trigger by which the metal wire of the tissue fastener 10 is restored in the loop shape without being entangled is formed at the side of the duodenum Dd. Thereby, step S10 ends and step S11 begins.

Step S11 is a step of separating the tissue fastener 10 from the applicator 20.

Figure 32:
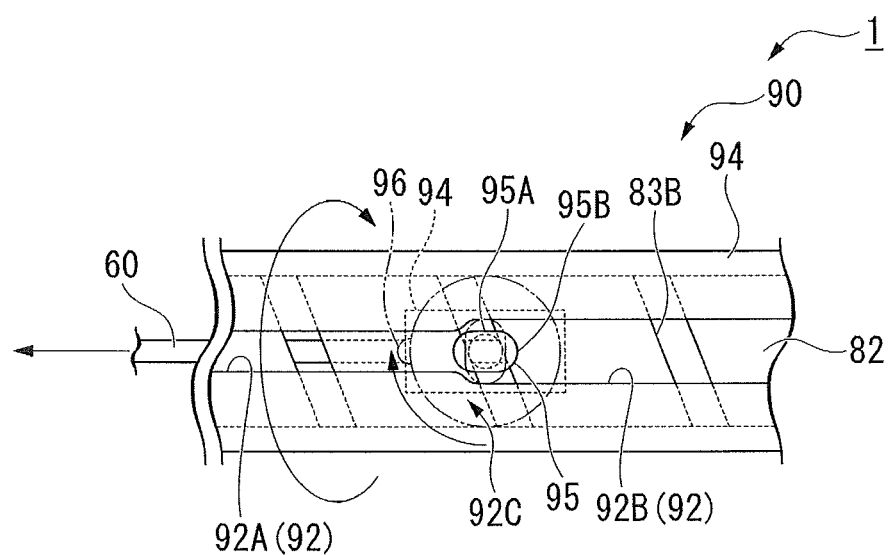
FIG. 32 is a motion explanatory view which shows the movement of the stylet operating part when the implant placement device according to the embodiment of the present invention is used.
Figure 33:
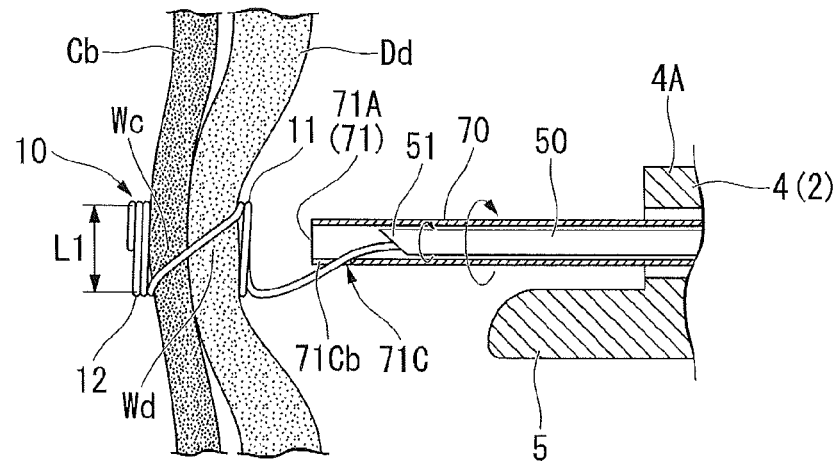
FIG. 33 is a motion explanatory view which shows the movement at the distal end side of the insertion part of the endoscope when the implant placement device according to the embodiment of the present invention is used.
Figure 34A:
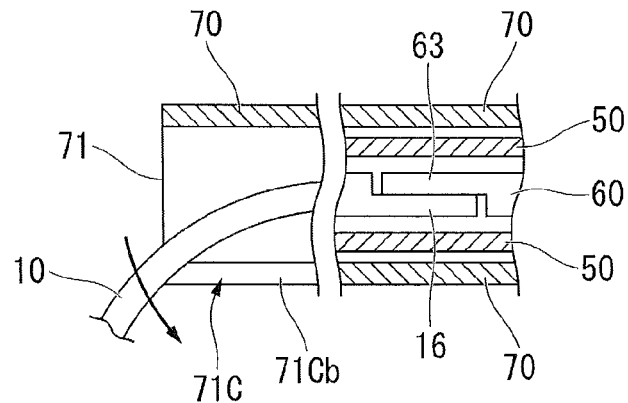
FIG. 34A is a motion explanatory view which shows motion of the distal end side of the sheath when the implant placement device according to the embodiment of the present invention is used.
Figure 34B:
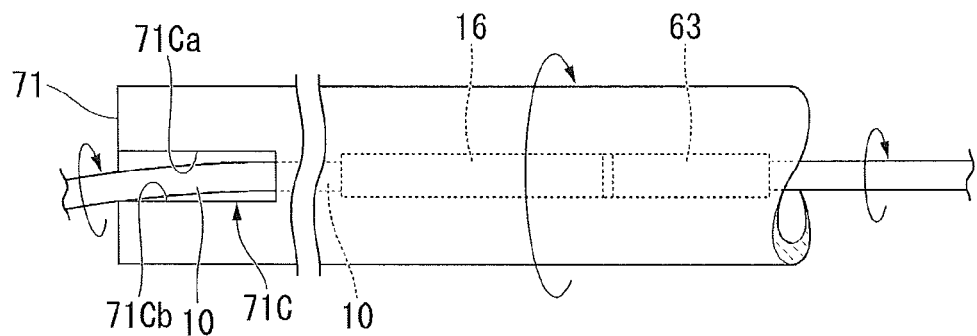
FIG. 34B is a motion explanatory view which shows the movement of the distal end side of the sheath when the implant placement device according to the embodiment of the present invention is used.
Figure 35:
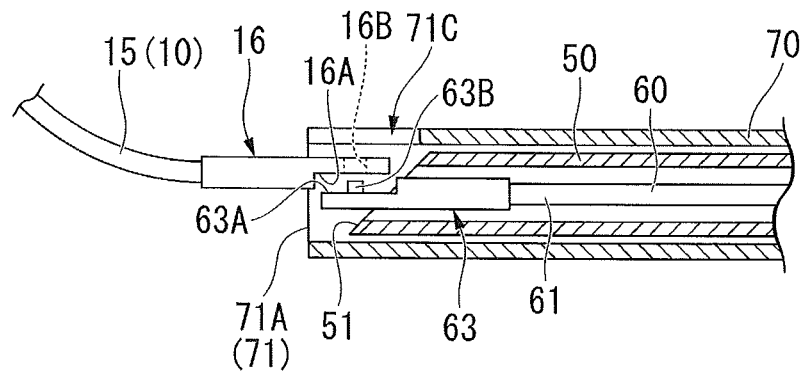
FIG. 35 is a motion explanatory view which shows the movement at the distal end side of the insertion part of the endoscope when the implant placement device according to the embodiment of the present invention is used.

In step S10 above, the metal wire of the tissue fastener 10 is exposed to the side of the duodenum Dd. Subsequently, in step S11, the metal wire is further unreeled from the tubular member 50 to the side of the distal end 51. FIG. 32 is a motion explanatory view to show the movement of the stylet operating part 90 when the implant placement device 1 is used. FIG. 33 is a motion explanatory view to show motion at the distal end side of the insertion part 4 of the endoscope 2 when the implant placement device 1 is used. FIGS. 34A and 34B are motion explanatory views to show motion of the side of the distal end 71 of the sheath 70 when the implant placement device 1 is used. FIG. 35 is a motion explanatory view to show motion at the distal end side of the insertion part 4 of the endoscope 2 when the implant placement device 1 is used.

First, as shown in FIG. 32, the user rotates the guide pin 95, which is located at the boundary 92C between the long holes 92A and 92B of the sheath tube 91 of the stylet operating part 90, around the axis of the guide pin 95 by 90 degrees. Then, the first wall portion 95A of the guide pin 95 is directed in the widthwise direction of the long hole 92, and the guide pin 95 is allowed to go into the long hole 92A.

Subsequently, similar to the movement in step S7, the user rotates the rotation input portion 93 relative to the operating body 41 in a rightward direction when the operating body 41 is viewed from the proximal end 41B toward the distal end 41A (see FIGS. 21 and 22). Here, since the first spiral cam 83A of the cam tube 82 is engaged with the fixing portion 81 of the tubular member operating part 80, the cam tube 82 does not rotate relative to the fixing portion 81. Similar to step S7, the cam tube 82 is rotated around the axis relative to the sheath tube 91. For this reason, as shown in FIG. 32, the fixing portion 94 fixed to the guide pin 95 relatively moves to the side of the distal end 91A of the sheath tube 91 along the second spiral cam 83B of the cam tube 82 as well as the long hole 92A of the sheath tube 91 while being rotated around the axis of the sheath tube 91.

Then, the stylet 60 fixed to the fixing portion 94 is rotated along with the fixing portion 94 in one body, and moves to the side of the distal end 91A of the sheath tube 91. Thereby, the stylet 60 is pushed out the tissue fastener 10 in the tubular member 50 to the side of the distal end 51 of the tubular member 50. Further, when the fixing portion 94 is rotated, the tubular member 50, the stylet 60, and the sheath 70 are interlocked with rotational motion around the axis by the rotation interlocking mechanism 110 coupled to the fixing portion 94, and are rotated as one body.

As shown in FIG. 33, the tissue fastener 10, which is unreeled from the distal end 51 of the tubular member 50 by the stylet 60, is restored at the side of the duodenum Dd in a coil shape by its own superelasticity. Here, in the distal end 71 of the sheath 70, the metal wire configuring the tissue fastener 10 is bent by its own superelasticity, and comes into contact with an opening end of the distal end 71 of the sheath 70.

Further, since the sheath 70 is rotated around the central axis of the sheath 70, as shown in FIG. 34A, the metal wire configuring the tissue fastener 10 goes into the notch 71C at any timing while the sheath 70 is rotated around the central axis of the sheath 70. After the metal wire configuring the tissue fastener 10 moves into the notch 71C, the metal wire is kept pressed against the wall part of the proximal end side in the notch 71C by its own superelasticity, and is held in the notch 71C. As a result, when the sheath 70 is rotated around the central axis of the sheath 70 after the metal wire configuring the tissue fastener 10 moves into the notch 71C, one of the pair of opposite surfaces 71Ca and 71Cb provided for the notch 71C (in the present embodiment, the opposite surface 71Cb that is a surface of a proximal side of the rotational direction of the sheath 70) rotates the metal wire around the central axis of the sheath 70 (see FIG. 34B).

The stylet 60 coupled with the tissue fastener 10 by the coupling portion 63 is integrally rotated along with the sheath 70 in the tubular member 50. For this reason, the tissue fastener 10 is rotated at two places by the pair of opposite surfaces 71Ca and 71Cb formed in the notch 71C and the coupling portion 63.

For example, when the notch 71C is not provided and the tissue fastener 10 is rotated only by the coupling portion 63, it is possible to rotate the coupling portion 16 that is kept coupled with the coupling portion 63. However, in the distal end 71 of the sheath 70, it is difficult for the tissue fastener 10 to be rotated. This is because the tissue fastener 10 is formed in a coil shape by the metal wire having superelasticity, and is disposed in the tubular member 50 or the sheath 70 in a stretched state. That is, due to a force that causes the metal wire configuring the tissue fastener 10 to be restored in the coil shape, an inner surface of the sheath 70 or an inner surface of the tubular member 50 is pushed by the tissue fastener 10. For this reason, a frictional force is applied between the inner surface of the sheath 70 and the tissue fastener 10 or between the inner surface of the tubular member 50 and the tissue fastener 10. As a result, when the tissue fastener 10 is rotated around the central axis of the sheath 70 or the tubular member 50, the metal wire is easily twisted, and it is difficult for a rotational force transmitted to the coupling portion 16 to be transmitted to the side of the distal end 71 of the sheath 70. Further, when the side of the distal end 51 of the tubular member 50 is bent, the metal wire is stably held in the tubular member 50 in a state in which a bent direction of the tubular member 50 and a bent direction of the metal wire are identical to each other. As such, a stronger force is required to rotate the metal wire around the central axis of the tubular member 50.

In contrast, in the present embodiment, a rotational force can be transmitted to the tissue fastener 10 using both the notch 71C formed in the distal end 71 of the sheath 70 and the coupling portion 63 installed on the stylet 60. For this reason, the tissue fastener 10 unreeled from the distal end 71 of the sheath 70 can be reliably rotated.

In this way, in step S11, when the metal wire is unreeled from the sheath 70 by one turn of the coil of the tissue fastener 10, the metal wire is rotated using the notch 71C formed in the distal end 71 of the sheath 70. Thereby, the metal wire can be prevented from being entangled at the side of the duodenum Dd, and the metal wire can be disposed in the coil shape.

As shown in FIG. 35, when the coupling portion 63 installed on the distal end 61 of the stylet 60 comes out of the distal end 51 of the tubular member 50, the coupling portion 16 supported by the inner wall of the tubular member 50 is no longer supported on the inner wall of the tubular member 50. Then, the through hole 16B of the coupling portion 16 is separated from the projection 63B of the coupling portion 63. Thereby, the tissue fastener 10 is separated from the applicator 20, and is placed in the body cavity.

If the tissue fastener 10 is placed in the body cavity, the stopper portion 26 of the coupling support 23 mounted on the operating part 3 of the endoscope 2 shown in FIG. 14 is demounted, and the implant placement device 1 is demounted from the endoscope 2. Further, the insertion part 4 of the endoscope 2 is withdrawn from the interior of the body cavity of a patient. Thereby, a series of procedures of placing the implant (tissue fastener 10) in the interior of the body cavity ends.

After the tissue fastener 10 is placed, an intestinal wall Wd of the duodenum Dd and a duct wall Wc of the common bile duct Cb, which are located in the basic loop L1 of the tissue fastener 10, are clamped by the first and second tissue fixing sections 11 and 12 (see FIG. 33). Thereby, in the duodenum Dd and the common bile duct Cb, portions inside the basic loop L1 cause pressure necrosis because a flow of blood is inhibited. Further, the intestinal wall Wd and the duct wall Wc are adhered around the basic loop L1.

Necrotized tissue and the tissue fastener 10 drop out of the placed position at which the tissue fastener 10 is placed. In this case, the first and second tissue fixing sections 11 and 12 are also always biased toward a lumen side of the duodenum Dd by the outer peripheral spring section 13. For this reason, when dropping out of other tissues, the tissue fastener 10 drops toward the lumen side of the duodenum Dd without fail. The tissue fastener 10 dropping to the lumen of the duodenum Dd is egested from the body through the small intestine and the large intestine. Here, since the coupling portion 16 extends toward the inward direction of the loop of the tissue fastener 10, when the tissue fastener 10 moves in the digestive canal, the coupling portion 16 comes into contact with the tissues, but causes no damage to the tissues.

For the purpose of restoring the tissue fastener in a coil shape without being twisted when the tissue fastener having the coil shape is used to bond living tissues, the wire (the metal wire, etc.) configuring the tissue fastener may be rotated around the central axis thereof. However, in the tubular member into which the tissue fastener is inserted in a stretched state, even when one end of the stretched tissue fastener is rotated, the other end of the stretched tissue fastener may not be rotated by friction between the tissue fastener and the tubular member. In particular, when the tubular member into which the tissue fastener is inserted in a stretched state is bent, a position of the tissue fastener is stabilized in a state in which a bent direction of the stretched tissue fastener and a bent direction of the tubular member are identical to each other. As such, it may be difficult to rotate the tissue fastener in the tubular member.

In contrast, in the implant placement device 1 of the present embodiment, the metal wire configuring the tissue fastener 10 can be rotated by the notch 71C formed in the distal end 71 of the sheath 70. As a result, the tissue fastener 10 can be correctly restored to the coil shape.

Further, when the tubular member and the sheath are configured to be relatively rotated to each other, there is a possibility of the inner wall of the sheath being chipped away by the distal end of the tubular member which is sharply formed. Chipped residues of the sheath which are generated in this case may be scattered in the body cavity such as the duodenum or the common bile duct, and unintended foreign materials may remain in the body cavity. In contrast, in the implant placement device 1 of the present embodiment, the rotational motions of the tubular member 50, the stylet 60, and the sheath 70 are always interlocked by the rotation interlocking mechanism 110. The rotational motions of the tubular member 50 and the sheath 70 are interlocked by the rotation interlocking mechanism 110. Thereby, the tubular member 50 and the sheath 70 are integrally rotated, and have a relation in which a circumferential relative position between the tubular member 50 and the sheath 70 is fixed. For this reason, by reducing movement by which the distal end 51 of the tubular member 50 chips away the inner wall of the sheath 70, it is possible to suppress the generation of the chipped residues of the sheath 70.

The three-layer coil sheath 53 is provided on the outer surface of the tubular member 50 so as to be interposed between the tubular member 50 and the sheath 70. In the present embodiment, since the three-layer coil sheath 53 is formed of a three-layered coil, the insertion part 30 can be smoothly bent in the forceps channel 7. Further, when the user manipulates the applicator 20 to rotate the insertion part 30, rotational followability of the insertion part 30 is high. Thereby, at the side of the endoscope 2, the movement of the user operation the applicator 20 can be transmitted to the distal end side of the insertion part 30 with high precision.

Since the stylet 60 is formed of a material having superelasticity, the insertion part 30 can be smoothly bent in the forceps channel 7. Further, when the user manipulates the applicator 20 to rotate the insertion part 30, the rotational followability of the insertion part 30 is high.

Since the tubular sheath slider 104 in which the cam groove 105 and the cam groove 106 are formed and the cam tube 102 in which the tilt cam groove 103 is formed are installed on the sheath operating part 100, the movement causing the sheath 70 to protrude to the side of the duodenum Dd and the movement pulling back the sheath 70 by a length shorter than a length corresponding to one turn of the basic loop L1 of the tissue fastener 10 can be continuously performed in that order. In this case, an amount by which the sheath 70 is protruded is determined by the length of the cam groove 105. The amount the sheath 70 is pulled back is determined by the distance between the ends 103A and 103B of the tilt cam groove 103 when the cam tube 102 is viewed in the longitudinal direction. For this reason, the sheath 70 can move forward/backward in an easy, correct way. As a result, the tissue fastener 10 can be reliably disposed at the side of the duodenum Dd.

After the sheath 70 protrudes to the side of the distal end 71, the sheath 70 is pulled back to the side of the proximal end 72. In this state, the sheath 70 protrudes from the distal end (protruding end) 5A of the ultrasonic observation part 5 installed on the insertion part 4 of the endoscope 2 to the side of the distal end 71 so as to be longer than the outer diameter of the third loop L3 of the tissue fastener 10. For this reason, in the movement of placing the tissue fastener 10 at the side of the duodenum Dd, the tissue fastener 10 can be inhibited from colliding with the endoscope even when the tissue fastener 10 moves unintentionally.

When the operating body 41 linearly moves along the cam groove 105 of the tubular sheath slider 104, the tubular member 50, the stylet 60, and the sheath 70 linearly move in one body. As such, the duodenum Dd and the common bile duct Cb are not clamped by the tissue fastener 10 and the sheath 70. For this reason, invasion on the living tissue can be reduced during the procedure of placing the tissue fastener 10. Further, since the tubular member 50 functions as a core in the sheath 70, deflection of the sheath 70 can be reduced. As a result, shake of the duodenum Dd pressed against the sheath 70 can be reduced, and the observation based on the optical observation mechanism is facilitated.

The elastic stopper 107 is formed on the tubular sheath slider 104. For this reason, after the sheath 70 is caused to protrude to the side of the distal end 71, the position of the sheath 70 can be maintained by resisting a force pushing back the sheath 70. For this reason, even when the user separates their hand from the applicator 20, the projection amount of the sheath 70 can be maintained.

The elastic stopper 108 is formed on the tubular sheath slider 104. For this reason, after the sheath 70 is pulled back to the side of the proximal end 72, even when the user separates their hand from the applicator 20, the pulling-back amount of the sheath 70 can be maintained.

When the sheath 70 is pulled back by the tubular sheath slider 104 and the cam tube 102, the operating body 41 as well as the stylet 60 and the tubular member 50 that follow the rotation of the operating body 41 are rotated as one body. For this reason, even when the tissue fastener 10 is unreeled from the distal end 71 of the sheath 70, the metal wire of the tissue fastener 10 can be inhibited from being entangled.

The winding direction of the tissue fastener 10 is a leftward direction, whereas the direction in which the tubular member 50, the stylet 60, and the sheath 70 are rotated is a rightward direction when viewed from the proximal end 52 toward the distal end 51 of the tubular member 50. To this end, the cams (the second spiral cam 83B and the tilt cam groove 103) are formed on the cam tube 82 and the cam tube 102. For this reason, when the tissue fastener 10 is unreeled from the distal end 51 of the tubular member 50, the metal wire of the tissue fastener 10 can be inhibited from being entangled. Alternatively, when the tissue fastener 10 is wound dextrally, the direction in which the tubular member 50, the stylet 60, and the sheath 70 are rotated may be a leftward direction when viewed from the proximal end 52 toward the distal end 51 of the tubular member 50. This can be easily changed in design by changing the shapes of the cams of the cam tubes 82 and 102 and the cam of the tubular sheath slider 104.

The pair of hooks 85 are installed on the tubular member slider 84 of the tubular member operating part 80, and the engaging groove 88B engaging the hooks 85 is formed in the slide stopper 87. For this reason, after the step of inserting the tubular member 50 into the tissues ends, the tubular member slider 84 is inhibited from unintentionally moving forward/backward in the longitudinal direction of the operating body 41.

The taper portion 88A is formed on the slide stopper 87. For this reason, the distal ends 85A of the hooks 85 pass over the taper portion 88A by the movement of pressing the tubular member slider 84 against the slide stopper 87. As such, the tubular member slider 84 and the slide stopper 87 can be fixed by pressing the tubular member slider 84 against the slide stopper 87.

After an insertion amount of the tubular member 50 is previously set by the slide stopper 87, the tubular member 50 is inserted into the tissues. For this reason, the tubular member 50 is not inserted farther than needed, and the puncturing length of the tubular member 50 is sufficient. As such, the tubular member 50 can be reliably punctured through the tissues, and there is no risk of other tissues being damaged by the tubular member 50.

The coupling screw 81C detachably coupling the tubular supporting member 81B of the fixing portion 81 and the cam tube 82 is provided. For this reason, when the coupling screw 81C is mounted, the forward/backward movement of the tubular member 50 can be interlocked with that of the stylet 60. When the coupling screw 81C is released, the tubular member 50 and the stylet 60 can be relatively moved. For this reason, when the tubular member 50 is pulled back to the side of the proximal end 52, the stylet relatively moves to the side of the distal end 51 of the tubular member 50, and the tissue fastener 10 can be unreeled from the distal end of the tubular member 50. For this reason, even when the tissue fastener 10 is pulled back, the first tissue fixing section 11 of the tissue fastener 10 is not pulled to the side of the duodenum Dd, and pressure against the living tissue of the side of the common bile duct Cb with which the first tissue fixing section 11 is in contact can be suppressed.

The tubular member 50 can be pulled back until the fixing portion 81 is displaced by the first spiral cam 83A and then the distal end 51 of the tubular member 50 fixed to the fixing portion 81 is located in the sheath 70. For this reason, after the tubular member 50 is pulled back, the sharp distal end 51 is not exposed to the outside. As such, there is no risk of other tissues being damaged by the distal end 51 of the tubular member 50.

According to the implant placing method of the present embodiment, the sheath 70 is displaced to the side of the distal end 71 in step S9, and thereby the duodenum Dd is pushed to the side of the common bile duct Cb. For this reason, the duodenum Dd and the common bile duct Cb can be brought into close contact with each other. As such, after the tissue fastener 10 is placed, the duodenum Dd and the common bile duct Cb can be reliably adhered.

In step S9, when the sheath 70 protrudes to the side of the distal end 71, the tubular member 50 and the stylet 60 protrude to the side of the distal end 71 along with the sheath 70. For this reason, the relative position of the tissue fastener 10 relative to the sheath 70 is not changed. Even when the sheath 70 is pressed against the duodenum Dd, there is no risk of the duodenum Dd and the common bile duct Cb being sandwiched by the tissue fastener 10 and the sheath 70.

In this case, the tubular member 50 can reinforce the sheath 70 from within the sheath 70 such that the sheath 70 is not bent. The duodenum Dd and the common bile duct Cb can be supported by resisting a force with which the sheath 70 is pushed back from the duodenum Dd or the common bile duct Cb.

After the sheath 70 protrudes to the side of the distal end 71 in step S9, the sheath 70 is pulled back to the side of the proximal end 72 in step S10. Thereby, the metal wire of the tissue fastener 10 is exposed from the distal end 71 of the sheath 70. For this reason, the metal wire of the tissue fastener 10 is bent at the side of the duodenum Dd by elasticity so as to be copied in its own loop shape in the order in which it is exposed from the distal end of the sheath 70. Thereby, at the side of the duodenum Dd, the shape of the tissue fastener 10 can be gradually restored from a portion adjacent to the duodenum Dd.

If the pulling-back amount of the sheath 70 is longer than one turn of the metal wire, there is a risk of the metal wire being restored in a coil shape at a position separated from the wall part of the duodenum Dd and forming an unintended loop, and the tissue fastener 10 becoming entangled. In the implant placing method of the present embodiment, the length by which the sheath 70 is pulled back to the side of the proximal end 72 is the length La, and is shorter than the length of the metal wire which corresponds to one circumferential turn of the basic loop L1 of the tissue fastener 10. For this reason, an unintended new loop is not formed by the movement of pulling back the sheath 70.

In step S10, even after the sheath 70 is pulled back to the side of the proximal end 72, the sheath 70 protrudes from the distal end 4A of the insertion part 4 of the endoscope 2 so as to be equal to or longer than a circumferential length of the third loop L3. For this reason, even when the tissue fastener 10 is unintentionally moved, the tissue fastener 10 can be inhibited from colliding with the endoscope 2.

In step S10, the movement of pulling back the sheath 70 to the side of the proximal end 72 is performed, and simultaneously the stylet 60 is rotated in the sheath 70. For this reason, the metal wire of the tissue fastener 10, which is exposed to the outside by pulling back the sheath 70 can be guided so as to be copied in the coil shape.

(Modification 1)

Hereinafter, a modification of the aforementioned implant placement device according to the one embodiment will be described.

In the present modification, the coupling portion 63 is not installed on the stylet 60, and the coupling portion 16 is not installed on the tissue fastener 10. That is, the stylet 60 is a rod-like member whose distal end is in contact with the proximal end of the tissue fastener 10 that is disposed inside the tubular member 50 in a stretched state. Accordingly, even when the stylet 60 is rotated around the central axis thereof, a rotational force by which the stylet 60 is rotated is not transmitted to the tissue fastener 10. For this reason, the stylet 60 has only a function of displacing the tissue fastener 10 to the side of the distal end 51 of the tubular member 50.

In the configuration shown in the present modification, the metal wire configuring the tissue fastener 10 can be rotated by the notch 71C formed in the distal end 71 of the sheath 70. With this configuration, it is not necessary to install the coupling portion coupling the stylet 60 and the tissue fastener 10. For this reason, in comparison with the configuration described in the one embodiment, the reliability with which the metal wire of the tissue fastener 10 is rotated is somewhat reduced, but the tissue fastener 10 can be correctly restored in a coil shape with a simple configuration.

(Modification 2)

Next, another modification of the aforementioned implant placement device according to the one embodiment will be described.

In the present modification, the tubular member 50 and the fixing member 81A are coupled so as to be partially rotatable around the central axis of the tubular member 50. Accordingly, in the case of the present modification, even when the fixing member 81A is rotated, the rotation of the fixing member 81A is not transmitted to the tubular member 50. For this reason, in the rotation interlocking mechanism 110, the rotational motion of the stylet 60 is interlocked with that of the sheath 70, but the rotational motions of the stylet 60 and the tubular member 50 are not interlocked with those of the sheath 70 and the tubular member 50.

With this configuration, similar to that described in the one embodiment, in steps S7 and S11, the tissue fastener 10 is interlocked with the rotation of the sheath 70, and can be rotated.

In the case of the present modification, the tubular member 50 is not interlocked with the rotational motions of the sheath 70 and the stylet 60. For this reason, in step S11, the tubular member 50 is not rotated. When the side of the distal end 51 of the tubular member 50 has a curved shape, the tubular member 50 should be rotated while the curved state of the side of the distal end 51 of the tubular member 50 is changed in order to rotate the tubular member 50 around the central axis of the tubular member 50, and a strong force is required. In contrast, in the present modification, a force for rotating the tubular member 50 is not required, and as such, the manipulation can be performed with a weak force.

(Modification 3)

Figure 36:
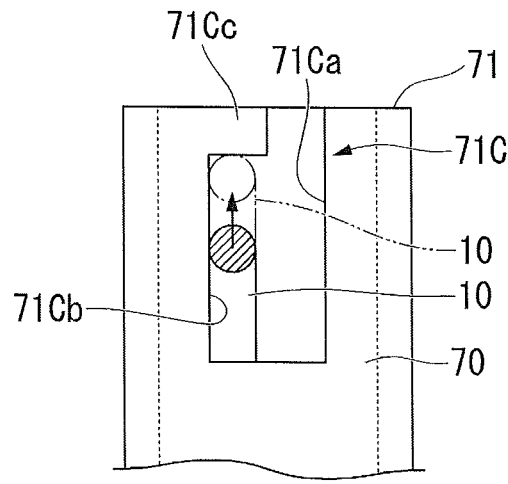
FIG. 36 is a plan view showing a configuration of a part of a modification of the implant placement device according to the embodiment of the present invention.

Next, another modification of the aforementioned implant placement device according to the one embodiment will be described with reference to FIG. 36. FIG. 36 is a plan view showing a distal end of a sheath in the implant placement device of the present modification.

As shown in FIG. 36, the present modification is different in that one of the pair of opposite surfaces 71Ca and 71Cb in the notch 71C is provided with a projection 71Cc protruding toward the other opposite surface. For example, when the rotational direction of the sheath 70 is a direction directed from the opposite surface 71Cb toward the opposite surface 71Ca, the projection 71Cc protruding from the opposite surface 71Cb toward the opposite surface 71Ca (i.e., from the opposite surface 71Cb located at the proximal side of the rotation direction of the sheath 70 toward the opposite surface 71Ca located at the distal side of the rotation direction of the sheath 70) is formed on the opposite surface 71Cb.

In the case of the present modification, when the metal wire configuring the tissue fastener 10 goes into the notch 71C from the distal end of the notch 71C, the metal wire moves in the rotational direction of the sheath 70 while in contact with the opposite surface 71Cb. Here, when an external force is applied to the metal wire or the applicator 20 moves, the metal wire is considered to move to the side of the distal end of the notch 71C. However, the metal wire is prevented from falling out of the notch 71C by the projection 71Cc formed on the opposite surface 71Cb. As a result, the number of rotations of the sheath 70 and the number of rotations of the tissue fastener 10 are prevented from varying, and the tissue fastener 10 can be more reliably restored in a coil shape.

(Modification 4)

Figure 37:
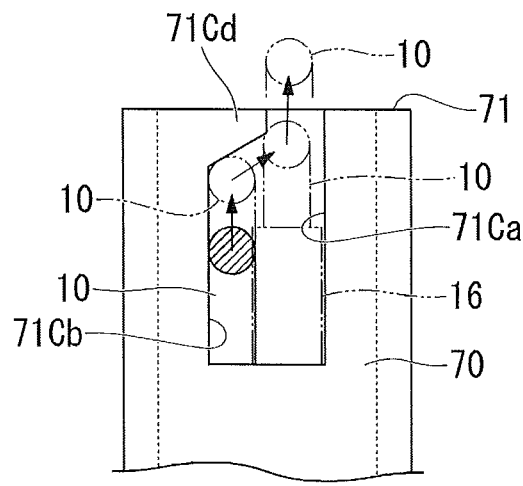
FIG. 37 is a plan view showing a configuration of a part of another modification of the implant placement device according to the embodiment of the present invention.

Next, another modification of the aforementioned implant placement device according to the one embodiment will be described with reference to FIG. 37. FIG. 37 is a plan view showing a distal end of a sheath in the implant placement device of the present modification.

As shown in FIG. 37, in the present modification, in place of the projection 71Cc, a projection 71Cd whose wall surface of the proximal end side is an inclined surface is provided. The wall surface of the proximal end side of the projection 71Cd is inclined so as to be directed in the rotational direction of the sheath 70 with the approach to the distal end of the sheath 70. Since this inclination is provided, when the tissue fastener 10 is rotated using the notch 71C of the distal end 71 of the sheath 70, the metal wire is also pushed to the proximal end side of the notch 71C by the inclined surface, and the tissue fastener 10 can be prevented from falling out of the notch 71C. Further, in the step of uncoupling the coupling portion 16 from the coupling portion 63, the metal wire comes into contact with the inclined surface of the projection 71Cd by the superelasticity of the tissue fastener 10. The metal wire is also guided to the opening portion of the distal end of the notch 71C along the inclined surface of the projection 71Cd. Thereby, the metal wire falls out of the notch 71C without being caught in the projection 71Cd, and the tissue fastener 10 is placed in the living tissue.

While exemplary embodiments of the invention have been described and illustrated above, it should be understood that the invention is not limited to these embodiments. Additions, omissions, substitutions, and other modifications can be made without departing from the spirit or scope of the present invention.

For example, in the aforementioned embodiment, the example in which the coil sheath 53 is the three-layered coil is shown. However, if the coil sheath 53 is a coil sheath having a plurality of layers of two or more layers, the effects of the present invention can be produced. When the number of layers of the coil sheath is increased, the outer diameter of the coil sheath is increased. As such, the number of layers of the coil sheath may be selected such that the outer diameter of the insertion part allows the tissue fastener 10 to be housed in the insertion part and allows the insertion part to be inserted into the forceps channel.

In the aforementioned embodiment, the example in which the tubular member 50 is formed of a uniform metal pipe is shown. Without being limited thereto, in place of the tubular member 50, a tubular member having a distal end tube part and a multilayered coil sheath fixed to a proximal end side of the distal end tube part may be employed. In this case, the tissue fastener 10 may be disposed inside the distal end tube part. The stylet 60 passes through the interior of the multilayered coil sheath to extend up to the fixing portion 94. According to this configuration, the rotation followability of the tubular member and the flexibility of the tubular member can be further increased.

In place of the tubular member 50 and the multilayered coil sheath, a tubular member having the aforementioned distal end tube part and an elastic tube part that is fixed to the proximal end side of the distal end tube part and has superelasticity may be employed. In this case, even when the forceps channel is complicatedly curved like the insertion part because the insertion part of the endoscope is complicatedly curved, the tubular member can be inhibited from undergoing plastic deformation. Further, the insertion part can be appropriately rotated in the forceps channel. In this case, the distal end tube part may also have superelasticity like the elastic tube part. All the parts of the tubular member may be integrally formed of a material having superelasticity. As an example of the material having superelasticity, for instance, a nickel titanium alloy may be employed.

In place of the tubular member 50 and the multilayered coil sheath, a tubular member having the aforementioned distal end tube part and a resin tube part that is fixed to the proximal end side of the distal end tube part and is formed of a resin may be employed. In this case, even when the forceps channel is complicatedly curved like the insertion part because the insertion part of the endoscope is complicatedly curved, the tubular member undergoes no plastic deformation. As such, the insertion part can be appropriately rotated in the forceps channel. In this case, the distal end tube part may also be formed of a resin like the resin tube part. However, when all the parts of the tubular member can be formed of a resin, the distal end of the tubular member is particularly sharply formed so as to be able to be inserted into the living tissue, or a perforation needs to be previously formed by another treatment tool.

In the aforementioned embodiment, only one notch may be formed in the distal end of the sheath. However, the number of notches in the distal end of the sheath is not limited to one. When only one notch is formed in the distal end of the sheath, it is difficult for the metal wire to be entangled because the metal wires do not go into a plurality of notches at the same time.

The aforementioned embodiment and each modification may be properly combined.

The invention is not limited by the above description, and is limited only by the scope of the appended claims.

What is claimed is:

1. An implant placement device used to place an implant formed of a coil-shaped metal wire into a tissue, the implant placement device comprising:
   a tubular member which has a lumen extending along a longitudinal axis of the tubular member such that the implant is disposed in a stretched state and an opening formed by communicating with the lumen;
   a stylet which is provided in the lumen so as to be movable in the lumen in a direction along the longitudinal axis in order to push the implant out of the tubular member;
   a sheath which is tubular, and provided so as to be rotatable around the longitudinal axis, and into which the tubular member is inserted;
   an operating body which is formed in an approximately tubular shape and provided at a proximal side of the sheath, wherein the operating body includes:
      a tubular member operating part which is provided to operate the tubular member;
      a stylet operating part which is provided to operate the stylet, the stylet being connected to the stylet operating part;
      a sheath operating part which is provided at the sheath and provided to operate the sheath; and
   a rotation interlocking mechanism which is provided to couple and rotate the stylet operating part and the sheath operating part around the longitudinal axis;
   a rotation input portion which is provided to be rotatable with respect to the operating body;
   a coupling portion which is formed at a distal end of the stylet, which is detachably coupled with a proximal end part of the implant, and which moves along with the stylet and the proximal end part of the implant in the direction along the longitudinal axis and is rotated around the longitudinal axis in accordance with the manipulation of the rotation input portion; and
   a notch which is provided at a distal end of the sheath, the notch being capable of accommodating at least part of the implant, the notch having an engaging surface to engage with the at least part of the implant in a state where the opening of the tubular member is located inside the sheath,
   wherein the notch is formed at a position such that the implant in a stretched state is capable of being engaged with both the notch and the coupling portion when the opening of the tubular member is located inside the sheath and the coupling portion is located inside the tubular member,
   wherein
   when the rotation input portion is rotated around the longitudinal axis, the sheath and the stylet are rotated in synchronization with each other around the longitudinal axis such that a circumferential relative positional relationship of the sheath, the stylet, and the implant is retained, and the stylet is moved toward the distal end of the sheath in the direction along the longitudinal axis by the rotation of the rotation input portion.

2. The implant placement device according to claim 1, wherein the notch opens at the distal end of the sheath, the notch includes a first surface and a second surface that are spaced apart from each other,
the first surface faces a rotation direction of the sheath, the second surface faces an opposite direction of that of the first surface,
the notch further has a projection that is formed on the first surface and protrudes from the first surface toward the second surface, and
a wire of the implant abuts the projection when the stretched implant is moved outside of the sheath and restored to a coil shape by rotating the sheath and the stylet and moving the stylet toward the distal end of the sheath.

3. The implant placement device according to claim 2, wherein a surface of a proximal end side of the projection is an inclined surface that is inclined so as to be directed in the rotational direction of the sheath with the approach to a distal end side of the sheath.

4. The implant placement device according to claim 1, wherein the notch is open on only one place in a distal end surface of the sheath.

5. The implant placement device according to claim 1, wherein the notch has a width greater than a diameter of the metal wire.

6. The implant placement device according to claim 1, wherein when the rotation input portion is rotated around the longitudinal axis, a distal end part of the implant receives a rotation force from the notch by engaging the implant to the engaging surface of the notch, and a proximal end part of the implant receives another rotation force from the coupling portion such that the sheath, the stylet, and the implant are rotated in synchronization with each other around the longitudinal axis.

7. The implant placement device according to claim 1, wherein the implant, which is in a stretched state between the notch and the coupling portion, is moved outside of the sheath while being restored to a coil shape by rotating the sheath and the stylet while moving the stylet toward the distal end of the sheath, in a state where the opening of the tubular member is located inside the sheath and the coupling portion is located inside the tubular member.

* * * * *